United States Patent
Gray et al.

(10) Patent No.: US 6,573,044 B1
(45) Date of Patent: Jun. 3, 2003

(54) METHODS OF USING CHEMICAL LIBRARIES TO SEARCH FOR NEW KINASE INHIBITORS

(75) Inventors: Nathanael S. Gray, Berkeley, CA (US); Peter Schultz, Oakland, CA (US); Lisa Wodicka, Santa Clara, CA (US); Laurent Meijer, Roscoff (FR); David J. Lockhart, Mountain View, CA (US)

(73) Assignees: The Regents of the University of California, Oakland, CA (US); Affymetrix, Inc., Santa Clara, CA (US); Centre National de la Recherche Scientifique, Paris (FR)

( * ) Notice: Subject to any disclaimer, the term of this patent is extended or adjusted under 35 U.S.C. 154(b) by 251 days.

(21) Appl. No.: 09/221,406

(22) Filed: Dec. 22, 1998

Related U.S. Application Data

(60) Provisional application No. 60/055,400, filed on Aug. 7, 1997, and provisional application No. 60/068,798, filed on Dec. 24, 1997.

(51) Int. Cl.$^7$ .................................................. C12Q 1/68
(52) U.S. Cl. .................. 435/6; 435/91.2; 435/DIG. 17; 544/268; 544/276; 544/277
(58) Field of Search .................... 435/6, 91.2, DIG. 17; 544/268, 276, 277

(56) References Cited

U.S. PATENT DOCUMENTS 5,866,702 A * 2/1999 Mackman et al. .......... 544/277
6,255,485 B1 * 7/2001 Gray et al. ................. 544/277

FOREIGN PATENT DOCUMENTS

| EP | 0 534 640 | 3/1993 |
|---|---|---|
| WO | WO 95/28169 | 10/1996 |
| WO | WO 97/16447 | 5/1997 |
| WO | WO 97/16452 A1 | 5/1997 |
| WO | WO 97/27317 | 7/1997 |
| WO | WO 97/42949 | 11/1997 |

OTHER PUBLICATIONS

Fodor, Science vol. 277 pp. 393 and 395, Jul. 1997.*
Havlicek, et al., *J. Med. Chem.*, 40:408–412 (1997).
Vesely, et al., *Eur. J. Biochem.*, 224:771–786 (1994).

* cited by examiner

*Primary Examiner*—Bennett Celsa
(74) *Attorney, Agent, or Firm*—Townsend & Townsend & Crew LLP

(57) ABSTRACT

The generation of selective inhibitors for specific protein kinases would provide new tools for analyzing signal transduction pathways and possibly new therapeutic agents. We have invented an approach to the development of selective protein kinase inhibitors based on the unexpected binding mode of 2,6,9-trisubstituted purines to the ATP binding site of human CDK2. The most potent inhibitor, purvalanol B ($IC_{50}$=6 nM), binds with a 30-fold greater affinity than the known CDK2 inhibitor, flavopiridol. The cellular effects of this class of compounds were examined and compared to those of flavopiridol by monitoring changes in mRNA expression levels for all genes in treated cells of *Saccharomyces cerevisiae* using high-density oligonucleotide probe arrays.

11 Claims, 6 Drawing Sheets

FLAVOPIRIDOL

OLOMOUCINE ($^1R = H$, $^2R = CH_3$)
ROSCOVITINE ($^1R = CH_2CH_3$, $^2R = CH(CH_3)_2$)

PURVALANOL A (R = H)
PURVALANOL B (R = $CO_2H$)

COMPOUND 40

COMPOUND 100 (R = $CH_3$)
101 (R = H)

METHODS OF USING CHEMICAL LIBRARIES TO SEARCH FOR NEW KINASE INHIBITORS

CROSS-REFERENCE TO RELATED APPLICATIONS

This application is related to, but does not claim priority to U.S. Provisional Patent Application No. 60/055,400, filed Aug. 7, 1997, which is herein incorporated by reference in its entirety. This application claims priority to U.S. Provisional Patent Application No. 60/068,798, filed Dec. 24, 1997, which is herein incorporated by reference in its entirety.

FEDERALLY SPONSORED RESEARCH AND DEVELOPMENT

This invention was supported by the Director, Office of Health Effects Research of the U.S. Department of Energy and by the National Science Foundation. The Government has certain rights in this invention.

BACKGROUND OF THE INVENTION

Phosphorylation of serine, threonine and tyrosine residues by protein kinases represents one of the most common post-translational regulatory modifications of proteins. More than 200 protein kinases have been described, following either purification to homogeneity or molecular cloning (see, Hunter, T. (1991), *Methods Enzymol.*, 200:3–37; Hanks, S. K., et al. (1991), *Methods Enzymol.*, 200:38–81; Hanks, S. K. 1991), *Curr. Opin. Struct. Biol.*, 1:369–383; and Hubbard, M. J., et al. (1993) *Trends Biochem. Sci.*, 18:172–177). It is thought that as much as 2–3% of eukaryotic genes encode protein kinases. The importance of protein kinases in physiological processes has stimulated an active search for specific inhibitors with potential pharmnacological interest (see, Hidaka, H., et al. (1992), *Annu. Rev. Pharmacol. Toxicol.*, 32:377–397). Several classes of compounds have been identified, such as staurosporine, naphthalene sulfonamides (W 7, ML-9, SC-9), isoquinoline derivatives (H-7, H-8, KN-62), sphingosine, tyrphostins and others, but in most cases these inhibitors display broad specificity. Only some pseudosubstrate autoinhibitory peptides show a high degree of specificity.

Cyclin-dependent kinases (CDK), in particular, have recently raised considerable interest in view of their essential role in the regulation of the cell division cycle (CDC) (see, Nigg, E. A. (1993), *Trends in Cell Biol.*, 3:296–301; and Sherr, C. S. (1993), *Cell*, 73:1059–1065). CDKs are highly conserved among eukaryotic species. Higher eukaryotic cells contain several isoforms of CDKs that become activated in specific phases of the cell cycle. CDKs consist of a catalytic subunit, the prototype of which is CDC2, and a regulatory subunit (cyclin). Six human CDK proteins have been described so far (see, Meyerson, M., et al. (1992), *EMBO J.*, 11:2909–2917; Meyerson, M., et al. (1994), *Mol. Cell. Biol.*, 14:2077–2086; and Van den Heuvel, S., et al. (1993), Science, 262:2050–2054), namely, CDK1 (also known as CDC2) and CDK2–6. With the exception of CDK3, for which the regulatory cyclin has not yet been identified, all these CDKs proteins are regulated by the transient association with one member of the cyclin family, i.e., cyclin A (CDC2, CDK2), B1–B3 (CDC2), D1–D3 (CDK2, CDK4, CDK5, CDK6), E (CDK2). Each step of the cell cycle is thought to be regulated by such CDK complexes: $G_1/S$ transition (CDK2/cyclin E, CDK3/unknown cyclin, CDK4/cyclin D1–D3, CDK6/cyclin D3), S phase (CDK2/cyclin A), $G_2$ (CDC2/cyclin A), $G_2/M$ transition (CDC2/cyclins B).

CDKs are able to phosphorylate many proteins involved in cell cycle events, including histones, lamins and tumor suppressor proteins, such as the retinoblastoma gene product pRb (see, Norbury, C., et al., supra, Matsushime, H., et al. (1992), *Cell*, 71:323–334, Nigg, E. E. (1993), *Curr. Opin. Cell. Biol.*, 5:187–193). In accordance with their central role in the cell cycle, enzyme activity is tightly controlled by multiple mechanisms. Kinase activation requires complex formation with regulatory cyclin proteins as described above, followed by an activating phosphorylation on Thr-161 in CDC2 or the corresponding Thr in the other CDKs (see, e.g., Gould, K. L., et al. (1991), *EMBO J.*, 10:3297–3309; Desai, D., et al. (1992), *Mol. Biol. Cell*, 3:571–582; Solomon, M. J., et al. (1992), *Mol. Biol. Cell*, 3:13–27). In addition, enzyme activity is negatively regulated by phosphorylations at Tyr-15 and/or Thr-14 (see, e.g., Solomon, M. J., et al., supra; Gu, Y., et al. (1992), *EMBO J.*, 11:3995–4005; Krek, W., et al. (1991), *EMBO J.*, 10:3331–3341; Norbury, C., et al. (1991), *EMBO J.*, 10:3321–3329; Parker, L. L., et al. (1992), *Proc. Nat'l. Acad. Sci. U.S.A.*, 89:2917–2921; McGowan, C. H., et al. (1993), *EMBO J.*, 12:75–85), or by complex formation with inhibitor proteins like p16 (see, Serrano, M., et al. (1993), *Nature*, 366:704–707; Kamb, A., et al. (1994), *Nature*, 264:436–440; Nobori, T., et al. (1994), *Nature*, 368:753–756), p27 (see, Polyak, K., et al. (1994), *Cell*, 78:59–66; Toyoshima, H., et al. (1994), *Cell*, 78:67–74), p28 (see, Hengst, L., et al. (1994), *Proc. Nat'l. Acad. Sci. U.S.A.*, 91:5291–5295) and p21 (see, Gu, Y., et al. (1993), *Nature*, 366:707–710; Xiiong, Y., et al. (1993), *Nature*, 366:701–704; Harper, J. W., et al. (1993), *Cell*, 75:805–816; Dulic, V., et al. (1994), *Cell*, 76:1013–1023), the latter being inducible by p53. Especially noteworthy is the fact that deletions of the p16 gene are found in over 50% of all human malignant cell lines tested (see, Kamb, A., supra, Nobori, T., et al., supra), although much less so in primary tumor cells (see, Spruck III, C. H., et al. (1994), *Nature*, 370:183–184), implicating p16 functions as tumor suppressor protein. Thus, both the cell growth signals transmitted through many oncogene products and the growth inhibitory signals from several tumor suppressor proteins modulate the activity of CDKs. Although mutations in CDKs themselves have not been associated with cancer, cyclin overexpression has been linked to tumorigenesis (see, Hunter, T., et al. (1991), *Cell*, 66:1071–1074; Keyomarsi, K., et al. (1993), *Proc. Nat'l. Acad. Sci. U.S.A.*, 90:1112–1116; Wang, T. C., et al. (1994), *Nature*, 369:669–671.) Hence, CDKs are a promising target for developing inhibitors with antineoplastic effects and for the treatment of cell-proliferative diseases.

The purine ring system is a key structural element of the substrates and ligands of many biosynthetic, regulatory and signal transduction proteins including cellular kinases, G proteins and polymerases. As such, the purine ring system has been a good starting point in the search for inhibitors of many biomedically significant processes. In fact, while screening purine analogs for inhibition of various protein kinases, a relatively selective inhibitor, olomoucine (FIG. 1), was identified that competitively inhibited CDK2/cyclin A with an $IC_{50}$ of 7 μM (see, Vesely, J., et al., (1994) *Eur. J. Biochem.*, 224:771–786). Further studies with olomoucine have demonstrated the orientation of the purine ring within the ATP-binding site of CDK2 is rotated almost 160 degrees relative to that of the adenosine ring of ATP. Consequently, it seems the introduction of new substituents at the 2, 6, and 9 positions of the purine ring rather than substituents appended to the ribose, as is normally done, might also selectively bind CDKs. There exists a need to rapidly screen compounds such as the trisubstituted purines to determine kinase inhibition. Quite surprisingly, the present invention satisfies such a need.

SUMMARY OF THE INVENTION

The present invention provides for methods of identifying compounds which modulate cell proliferation. The methods comprise the steps of (i) treating at least one cell with at least one compound, (ii) isolating a plurality of mRNA transcripts from said cell, and (iii) comparing a plurality of mRNA transcripts from a cell not treated with the compound to the mRNA transcripts from the treated cell, whereby a de in the number of mRNA transcripts indicates an inhibition of cell proliferation. In one embodiment of the invention, the compounds are inhibitors of cyclin-dependent kinases. In another embodiment, the mRNA transcripts are converted to cRNA. In yet another embodiment, the mRNA transcripts encode proteins associated with cell proliferation. Finally, in another embodiment, the mRNA is isolated by hybridization under stringent conditions to oligonucleotide probes of about 15 to about 50 nucleotides complementary to nucleic acids which encode proteins associated with cell proliferation. In a particularly preferred embodiment, the oligonucleotides are linked to a solid support in a high density array.

In another aspect of the invention, a method of determining the identity of proteins that modulate cell proliferation during or posure to chemical or genetic challenges is provided. The method comprises the steps of (i) isolating mRNA transcripts generated from cells after exposure to compounds known to modulate cellular proliferation, (ii) isolating mRNA transcripts generated from cells not exposed to said compounds, (iii) comparing the total number of mRNA transcripts from both treated and untreated cells, and (iv) determining which proteins are encoded by mRNA transcripts present in differing amounts in treated or untreated cells. In one embodiment of this aspect, the compounds are cyclin-dependent kinase inhibitors. In another embodiment, the mRNA transcripts are converted to cRNA. In still another embodiment, the mRNA is isolated by hybridization under stringent conditions to oligonucleotides of about 15 to about 50 nucleotides in length which are complementary to nucleic acids that encode proteins associated with cell proliferation. In a particularly preferred embodiment, the oligonucleotides are linked to a solid supporte in a high density array.

In a final aspect of this invention, a method of determining proteins associated with increased drug resistance is provided. The method comprises the steps of (i) isolating mRNA transcripts generated from drug-resistant cells after exposure to drugs known to inhibit cellular proliferation, (ii) isolating mRNA transcripts generated from non-drug resistant cells exposed to said drugs, (iii) comparing the total number of mRNA transcripts from both drug-resistant and non-resistant cells, and (iv) determining which proteins are encoded by mRNA transcripts present in increased amounts in the drug-resistant cells. In one embodiment, the compounds are cyclin-dependent kinase inhibitors. In another embodiment, the mRNA transcripts are converted to cRNA. In still another embodiment, the mRNA is isolated by hybridization under stringent conditions to oligonucleotides of about 15 to about 50 nucleotides in length which are complementary to nucleic acids that encode proteins associated with cell proliferation. In a particularly preferred embodiment, the oligonucleotides are linked to a solid supporte in a high density array.

Other features, objects and advantages of the invention and its preferred embodiments will become apparent from the detailed description which follows.

DETAILED DESCRIPTION OF THE INVENTION

Figure 1:
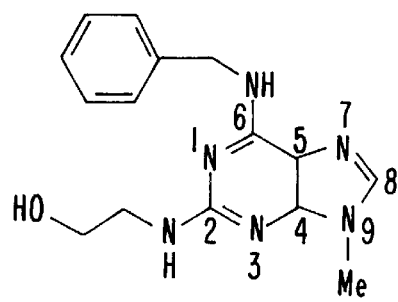
FIG. 1 sets forth the structure of olomoucine and the numbering scheme for the purine nucleus.

The present invention provides a combinatorial approach to modifying the purine scaffold to better aid in the search for potent and specific inhibitors of various purine-utilizing enzymes. The central role that purine utilizing enzymes, in particular, cyclin-dependent kinases (CDKs), play in controlling cell division, and the high incidence of CDK alteration, or of deregulation of endogenous CDK inhibitors such as p21$^{Cip1}$, WAF-1 and p27$^{Kip1}$ (Polyak, et al., *Cell* 78, 59–66 (1994); and Toyoshima & Hunter, *Cell* 78, 67–74 (1994)) in a number of cancers, make CDKs an excellent target for the design of selective inhibitors.

During cellular differentiation, CDK/cyclin complexes are negatively regulated in response to a variety of antiproliferative signals including myogenic (Parker, *Science* 59:66 (1994)), myeloid (Liu, et al., *Genes Dev.* 10, 142–153 (1996)), contact inhibition, and DNA damage checkpoints (El-Deiry, *Cell* 75, 817–825 (1993)).

Workers in the field have recognized a variety of possible routes towards inhibition of CDKs: prevention of phosphorylation by CDK activating kinase (CAK), induction of expression of CDK inhibitors (Kip/Cip and INK4 family), inhibition of ATP or protein substrate binding, interference with intracellular localization, or interference with cyclin binding. In this invention, the ATP binding site was targeted by screening combinatorial libraries of 2,6,9-trisubstituted purines. This strategy was motivated by the unexpected binding mode of the purine olomoucine, which exhibited good selectivity but moderate inhibition [IC$_{50}$ (50% kinase inhibition)=7 $\mu$M] of a subset of the members of CDK family of protein kinases (Vesely, et al., *Eur. J. Biochem.* 224:771–786 (1994); and Schulze-Gahmen, et al., *Proteins* 22:378–391 (1995)). A combinatorial approach to modifying the purine scaffold could be of widespread utility in the search for potent and specific inhibitors of various cellular processes due to the ubiquitous occurrence of purine-utilizing enzymes, including the estimated 2000 kinases encoded in the human genome.

DEFINITIONS

The term "independently selected" is used herein to indicate that the R groups, e.g., $R^1$, $R^2$, $R^4$ and $R^5$, can be identical or different (e.g., $R^1$, $R^2$ and $R^3$ may all be substituted alkyls or $R^1$ and $R^2$ may be a substituted alkyl and $R^3$ may be an aryl, etc.)

A named R group will generally have the structure which is recognized in the art as corresponding to R groups having that name. For the purposes of illustration, representative R groups as enumerated above are defined herein. These definitions are intended to supplement and illustrate, not preclude, the definitions known to those of skill in the art.

The term "alkyl" is used herein to refer to a branched or unbranched, saturated or unsaturated, monovalent hydrocarbon radical having from 1–12 carbons and preferably, from 1–6 carbons. When the alkyl group has from 1–6 carbon atoms, it is referred to as a "lower alkyl." Suitable alkyl radicals include, for example, methyl, ethyl, n-propyl, i-propyl, 2-propenyl (or allyl), n-butyl, t-butyl, i-butyl (or 2-methylpropyl), etc.

"Substituted alkyl" refers to alkyl as just described including one or more functional groups such as lower alkyl, aryl, acyl, halogen (i.e., alkylhalos, e.g., CF$_3$), hydroxy, amino, alkoxy, alkylamino, acylamino, acyloxy, aryloxy, aryloxyalkyl, mercapto, both saturated and unsaturated cyclic hydrocarbons, heterocycles and the like. These groups may be attached to any carbon of the alkyl moiety.

The term "aryl" is used herein to refer to an aromatic substituent which may be a single aromatic ring or multiple aromatic rings which are fused together, linked covalently, or linked to a common group such as a methylene or ethylene moiety. The common linking group may also be a carbonyl as in benzophenone. The aromatic ring(s) may include phenyl, naphthyl, biphenyl, diphenylmethyl and benzophenone among others.

The term "arylalkyl" is used herein to refer to a subset of "aryl" in which the aryl group is attached through an alkyl group as defined herein.

"Substituted aryl" refers to an aryl as just described and including one or more functional groups such as lower alkyl, acyl, halogen, alkylhalos (e.g., CF$_3$), hydroxy, amino, alkoxy, alkylamino, acylamino, acyloxy, mercapto and both saturated and unsaturated cyclic hydrocarbons fused to the aromatic ring(s), linked covalently or linked to a common group such as a methylene or ethylene moiety. The linking group may also be a carbonyl such as in cyclohexyl phenyl ketone. The term "substituted aryl" encompasses "substituted arylalkyl."

"Substituted arylalkyl" defines a subset of "substituted aryl" wherein the substituted aryl group is attached through an alkyl group as defined herein.

The term "halogen" is used herein to refer to fluorine, bromine, chlorine and iodine atoms.

The term "hydroxy" is used herein to refer to the group COH.

The term "amino" is used herein to refer to the group CNRRN, where R and RN may independently be hydrogen, lower alkyl, substituted lower alkyl, aryl, substituted aryl or acyl.

The term "alkoxy" is used herein to refer to the COR group, where R is a lower alkyl, substituted lower alkyl, aryl, substituted aryl, arylalkyl or substituted arylalkyl wherein the alkyl, aryl, substituted aryl, arylalkyl and substituted arylalkyl groups are as described herein. Suitable alkoxy radicals include, for example, methoxy, ethoxy, phenoxy, substituted phenoxy, benzyloxy, phenethyloxy, t-butoxy, etc.

The term "alkylamino" denotes secondary and tertiary amines wherein the alkyl groups may be either the same or different and may consist of straight or branched, saturated or unsaturated hydrocarbons.

The term "heterocyclic" is used herein to describe a monovalent group having a single ring or multiple condensed rings from 1–12 carbon atoms and from 1–4 heteroatoms selected from nitrogen, sulfur or oxygen within the ring. Such heterocycles are, for example, tetrahydrofuran, morpholine, piperidine, pyrrolidine, thiophene, pyridine, isoxazole, phthalimide, pyrazole, indole, furan, benzo-fused analogs of these rings, etc.

The term "substituted heterocyclic" as used herein describes a subset of "heterocyclic" wherein the heterocycle nucleus is substituted with one or more functional groups such as lower alkyl, acyl, halogen, alkylhalos (e.g., CF$_3$), hydroxy, amino, alkoxy, alkylamino, acylamino, acyloxy, mercapto, etc.

The term "pharmaceutically acceptable salt" refers to those salts of compounds which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutically acceptable salts include, for example, alkali metal salts, such as sodium and potassium, alkaline earth salts and ammonium salts.

The term "contacting" is used herein interchangeably with the following: combined with, added to, mixed with, passed over, incubated with, flowed over, etc. Moreover, the purine compounds of present invention can be "administered" by any conventional method such as, for example, parenteral, oral, topical and inhalation routes as described herein.

"An amount sufficient" or "an effective amount" is that amount of a given purine analog which exhibits the binding/inhibitory activity of interest or, which provides either a subjective relief of a symptom(s) or an objectively identifiable improvement as noted by the clinician or other qualified observer.

"Complementary" refers to the topological compatibility or matching together of interacting surfaces of a ligand molecule and its receptor. Thus, the receptor and its ligand can be described as complementary, and furthermore, the contact surface characteristics are complementary to each other.

A "ligand" is a molecule that is recognized by a particular receptor. Examples of ligands that can be investigated by this invention include, but are not restricted to, cRNA, mRNA and other oligonucleotides, agonists and antagonists for cell membrane receptors, toxins and venoms, viral epitopes, hormones (e.g., steroids, etc.), hormone receptors, peptides, enzymes, enzyme substrates, cofactors, (e.g., opiates, etc.), lectins, sugars, oligosaccharides, proteins, and monoclonal antibodies.

"Nucleic acids" include DNA and RNA, as well as individual nucleotides and oligonucleotides. One subset of RNA is mRNA. The complement of mRNA is cRNA. Its preparation is well known to those of skill and is described in Gray, et al., *Science* 281:533 (1998) which is hereby incorporated in its entirety for all purposes. For purposes of this invention cRNA is used synonymously with mRNA.

As used herein, "stringent hybridization conditions" or "stringency" refers to conditions in a range from about 5° C. to about 20° C. or 25° C. below the melting temperature (Tm) of the target sequence and a probe with exact or nearly exact complementarity to the target. As used herein, the melting temperature is the temperature at which a population of double-stranded nucleic acid molecules becomes half-dissociated into single strands. Methods for calculating the Tm of nucleic acids are well known in the art (see, e.g., Berger and Kimmel (1987) *Methods In Enzymology, Vol. 152: Guide To Molecular Cloning Techniques*, San Diego: Academic Press, Inc. and Sambrook et al. (1989) *Molecular Cloning: A Laboratory Manual, 2nd Ed., Vols.* 1–3, Cold Spring Harbor Laboratory hereinafter, "Sambrook"), both incorporated herein by reference). As indicated by standard references, a simple estimate of the Tm value may be calculated by the equation: Tm=81.5+0.41(% G+C), when a nucleic acid is in aqueous solution at 1 M NaCl (see e.g., Anderson and Young, Quantitative Filter Hybridization in *Nucleic Acid Hybridization* (1985)). Other references include more sophisticated computations which take structural as well as sequence characteristics into account for the calculation of Tm. The melting temperature of a hybrid (and thus the conditions for stringent hybridization) is affected by various factors such as the length and nature (DNA, RNA, base composition) of the probe and nature of the target (DNA, RNA, base composition, present in solution or immobilized, and the like), and the concentration of salts and other components (e.g., the presence or absence of fornamide, dextran sulfate, polyethylene glycol). The effects of these factors are well known and are discussed in standard references in the art, see e.g., Sambrook; *Current Protocols In Molecular Biology*, Ausubel, ed. John Wiley & Sons, Inc., New York (1997) ("Ausubel"). Typically, stringent hybridization conditions are salt concentrations less than about 1.0 M sodium ion, typically about 0.01 to 1.0 M sodium ion at pH 7.0 to 8.3, and temperatures at least about 30° C. for short probes (e.g., 10 to 50 nucleotides) and at least about 65° C. for long probes (e.g., greater than 50 nucleotides). As noted, stringent conditions may also be achieved with the addition of destabilizing agents such as formamide, in which case lower temperatures may be employed.

The term "genetic challenge" refers to an aberration in the DNA of the cell. An example of a genetic challenge is a mutation, either a single nucleotide exchange, an addition of one or more nucleotides, or a deletion of one or more nucleotides. Mutations are induced by techniques well known in the art, e.g., UV irradiation, and exposure to compounds known to cause knicks and cuts in either one or both strands of DNA.

Chemical challenges are the addition of compounds which, in addition to causing mutations in DNA also cause aberrations in cell proliferation, metabolism and catabolism. Such compounds include, but are not limited to, the purine analogs of this invention.

For purposes of this invention, a "receptor" is a molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, oligonucleotides, cell membrane receptors, monoclonal antibodies and antisera reactive with specific antigenic determinants (such as on viruses, cells or other materials), drugs, sugars, polysaccharides, cells, cellular membranes, and organelles. Receptors are sometimes referred to in the art as anti-ligands. As the term receptors is used herein, no difference in meaning is intended. A "ligand receptor pair" is formed when two macromolecules have combined through molecular recognition to form a complex.

"Monomer" is a member of the set of small molecules which can be joined together to form a polymer. The set of monomers includes but is not restricted to, for example, the set of common nucleotides, the set of synthetic nucleotides, the set of nucleotide analogs and the set of pentoses and hexoses. As used herein, monomers refers to any member of a basis set for synthesis of a polymer. For example, dimers of nucleotides form a basis set of 400 monomers for synthesis of polypeptides. Different basis sets of monomers may be used at successive steps in the synthesis of a polymer.

"Radiation" is energy which may be selectively applied including energy having a wavelength of between $10^{-14}$ and $10^4$ meters including, for example, electron beam radiation, gamma radiation, x-ray radiation, ultraviolet radiation, visible light, infrared radiation, microwave radiation, and radio waves. "Irradiation" refers to the application of radiation to a surface.

The term "substrate" refers to a material having a rigid or semi-rigid surface. In many embodiments, at least one surface of the substrate will be substantially flat, although in some embodiments it may be desirable to physically separate synthesis regions for different polymers with, for example, wells, raised regions, etched trenches, or the like. According to other embodiments, small beads may be provided on the surface which may be released upon completion of the synthesis.

The phrase "protective group" refers to a material which is bound to a monomer unit and which may be spatially removed upon selective exposure to an aciator such as electromagnetic radiation. Examples of protective groups with utility herein include nitroveratryloxy carbbnyl, nitrobenzyloxy carbonyl, dimethyl dimethoxybenzyloxy carbonyl, 5 -bromo-7-nitroindolinyl, o-hydroxy- alpha -methyl cinnamoyl, and 2-oxymethylene anthraquinone. Other examples of activators include ion beams, electric fields, magnetic fields, electron beams, x-ray, and the like.

The phrase "predefined region" refers to a predefined region is a localized area on a surface which is, was, or is intended to be activated for formation of a polymer. The prede fined region may have any convenient shape, e.g. circular, rectangular, elliptical, wedge-shaped, etc. For the sake of brevity herein, "predefined regions" are sometimes referred to simply as "regions."

The phrase "substantially pure" refers to a polymer that is considered to be "substantially pure" within a prede fined region of a substrate when it exhibits characteristics that distinguish it from other predefined regions. Typically, purity will be measured in terms of biological activity or function as a result of uniform sequence. Such characteristics will typically be measured by way of binding with a selected ligand or receptor.

PURINE ANALOGS

The purine ring is a key structural element of the substrates and ligands of many biosynthetic, regulatory and signal transduction proteins including cellular protein kinases, G proteins and polymerases. Quite importantly, the present invention provides purine analogs which can be used to inhibit such proteins and, thus, many biomedically important processes. More particularly, the present invention provides purine analogs that inhibit, inter alia, protein kinases and other cellular processes. As such, the purine analogs of the present invention can be used to block cell-cycle progression, cellular proliferation, and apoptosis as well as other cellular processes. The purine analogs of the present invention are active in the subnanomolar and submicromolar ranges.

In one aspect of one embodiment, the present invention provides for methods of screening purine analogs having the generally formula:

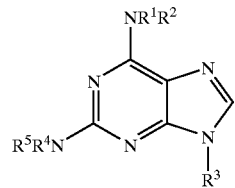

I or a pharmaceutically acceptable salt thereof.

In Formula I, $R^1$, $R^2$, $R^4$ and $R^5$ are independently selected and are functional groups including, but not limited to, H, $C_1$–$C_8$ straight-chain, branched-chain, saturated and unsaturated alkyl, $C_1$–$C_8$ straight-chain, branched-chain, saturated and unsaturated substituted alkyl, aryl and substituted aryl.

Within the scope of the above Formula I, certain embodiments are preferred, namely those in which $R^1$ and $R^2$ are independently selected and are functional groups including, but not limited to, H, aryl, substituted aryl, $C_1$–$C_8$ straight-chain, saturated alkyl substituted with aryl and $C_1$–$C_8$ straight-chain, saturated alkyl substituted with substituted aryl; $R^3$ is a functional group including, but not limited to, $C_1$–$C_8$ branched-chain saturated alkyl and $C_1$–$C_8$ branched-chain unsaturated alkyl; and $R^4$ and $R^5$ are independently selected and are functional groups including, but not limited to, H, $C_1$–$C_8$ straight-chain, branched-chain, saturated and unsaturated alkyl, $C_1$–$C_8$ straight-chain, branched-chain, saturated and unsaturated substituted alkyl, aryl and substituted aryl.

In another preferred embodiment, $R^1$ and $R^2$ are independently selected and are functional groups including, but not limited to, H, unsubstituted aryl and substituted aryl; $R^3$ is isopropyl; and $R^4$ and $R^5$ are independently selected and are functional groups including, but not limited to, H, $C_1$–$C_8$ saturated and unsaturated branched-chain alkyl and $C_1$–$C_8$ saturated and unsaturated branched-chain substituted alkyl.

In another preferred embodiment, $R_4$ and $R_5$ are independently selected and are functional groups including, but not limited to, H, and

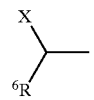

wherein X is a member selected from the group consisting of H, OH, $CH_2OH$, $C(O)NH_2$, SH, COOH or a pharmaceutically acceptable salt thereof, and $COOR^7$, wherein $R^7$ is lower alkyl; and $R^6$ is a member selected from the group consisting of H, $C_1$–$C_8$ straight-chain alkyl, $C_1$–$C_8$ branched-chain alkyl, $C_1$–$C_8$ straight-chain substituted alkyl, $C_1$–$C_8$ branched-chain substituted alkyl.

With respect to the above embodiment, X is preferably COOH; and $R^6$ is independently selected and is a functional group including, but not limited to, H, —$CH_3$, —$(CH_2)_3$ $NHC(=NH)NH_2$, —$CH_2CONH_2$, —$CH_2CO_2H$, —$CH_2SH$, —$(CH_2)_2CONH_2$, —$(CH_2)_2CO_2H$, —$CH_2$(4-imidazoyl), —$CH(CH_3)CH_2CH_3$, —$CH_2CH(CH_3)_2$, —$(CH_2)_2SCH_3$, —$CH_2Ph$, —$CH_2OH$, —$CH(CH_3)OH$, —$CH_2$(3-indolyl), —$CH_2$(4-hydroxy phenyl) and —$CH(CH_3)_2$.

In such embodiments, $R^1$ and $R^2$ are independently selected and are functional groups including, but not limited to, H and aryl substituted in at least one of positions 3, 4, or 5 with a member independently selected from the group consisting of halogen, alkoxy, trihalomethyl, amino, hydroxyl, thiol, sulfonic acid, sulfonic acid, amide, ester and carboxylic acid.

Table 1 sets forth purine compounds in accordance with the present invention which are particularly preferred. The compounds in this table and throughout this specification are referred to by code numbers, which are used for convenience only, and are strictly arbitrary for purposes of this invention.

TABLE 1

Exemplary Purine Analogs

| Structure | Code Name | IC$_{50}$ cdc2/cyclin B (additional kinases) |
|---|---|---|
| Class 1 | | |
| 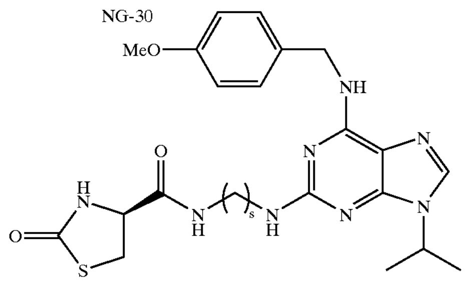 | NG-30 | 330 nM<br>2000 nM (CDK2/cyclin E)<br>>33,000 nM (GSK-3)<br>8,000 nM (erk1) |
| Class 2a | | |
| 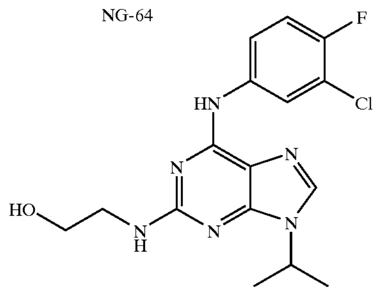 | NG-64 | 290 nM |
| 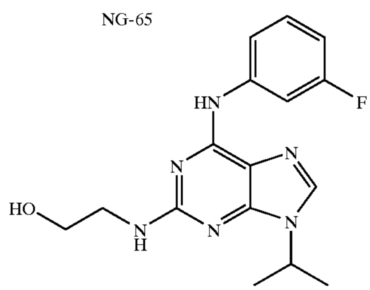 | NG-65 | 400 nM |
| 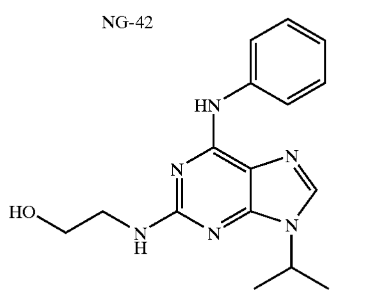 | NG-42 | 4300 nM |

TABLE 1-continued

Exemplary Purine Analogs

| Structure | Code Name | IC$_{50}$ cdc2/cyclin B (additional kinases) |
|---|---|---|
| 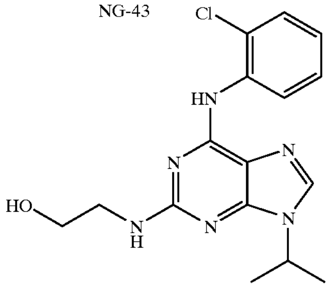 | NG-43 | 4300 Nm |
| 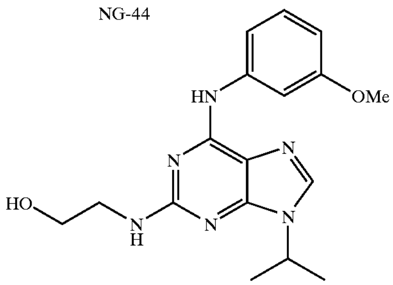 | NG-44 | 500 nM |
| 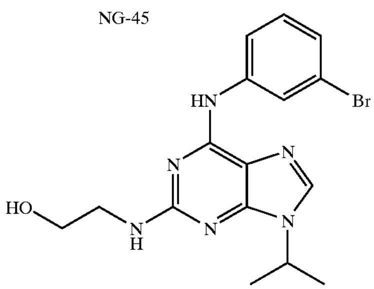 | NG-45 | 270 nM |
| 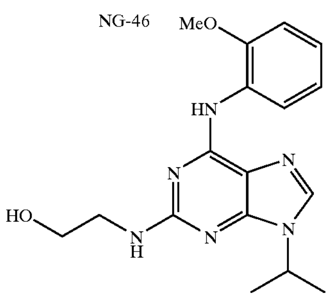 | NG-46 | 9000 nM |
| 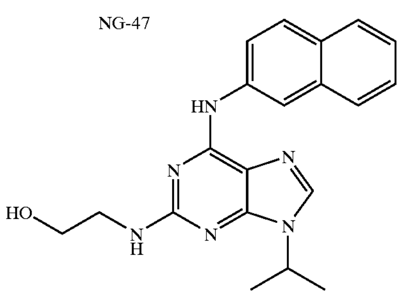 | NG-47 | 430 nM |

TABLE 1-continued

Exemplary Purine Analogs

| Structure | Code Name | IC$_{50}$ cdc2/cyclin B (additional kinases) |
|---|---|---|
| 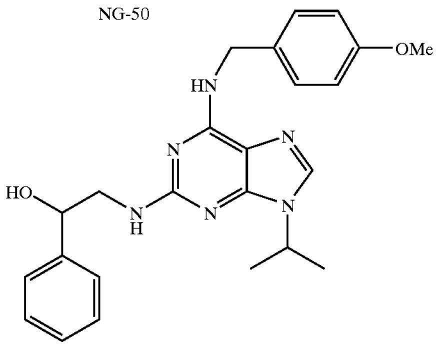 | NG-50 | 2800 nM |
| 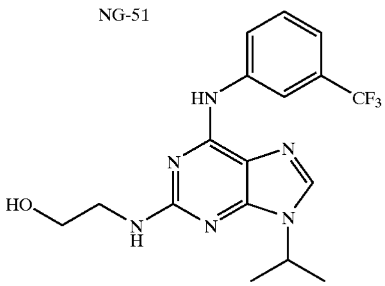 | NG-51 | 420 nM |
| 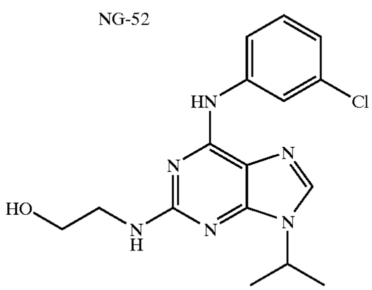 | NG-52 | 220 nM |
| 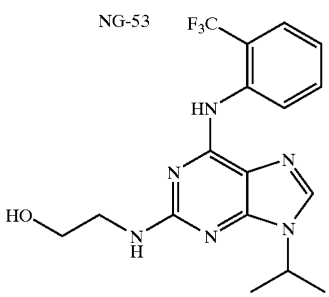 | NG-53 | 10,000 nM |
| 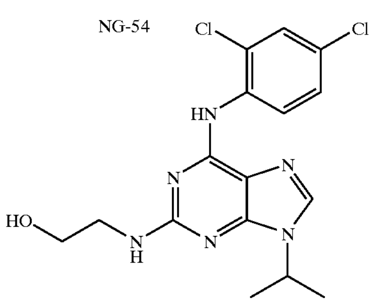 | NG-54 | 2700 nM |

TABLE 1-continued

Exemplary Purine Analogs

| Structure | Code Name | IC$_{50}$ cdc2/cyclin B (additional kinases) |
|---|---|---|

Class 2b

NG-35

150 nM
140 (cdk2/cyclin E)
15 nM (cdk5/p25)
4500 (GSK-3)
3000 (erk1)

NG-76

600 nM
400 (CDK2/cyclin E)

NG-75

230 nM
150 (DK2/cyclin E)

NG-33

130 nM
80 nM (CDK2/cyclin E)
20,000 nM (GSK-3)
>10,000 nM (erk1)

NG-36

100 nM
100 nM (CDK2/cyclin E)
13,000 nM (GSK-3)
>10,000 nM (erk1)

TABLE 1-continued

Exemplary Purine Analogs

| Structure | Code Name | IC$_{50}$ cdc2/cyclin B (additional kinases) |
|---|---|---|

Class 2c

NG-16

240 nM
180 nM (CDK2/cyclin E)
23,000 nM (GSK-3)
>50,000 nM (erk1)

NG-26

330 nM
230 nM (CDK2/cyclin E)
>33,000 nM (GSK-3)
33,000 nM (erk1)

NG-40

600 nM

NG-49

2800 nM

TABLE 1-continued

Exemplary Purine Analogs

| Structure | Code Name | IC$_{50}$ cdc2/cyclin B (additional kinases) |
|---|---|---|

Class 3

NG-60

35 nM
30 nM (CDK2/cyclin E)

NG-56

35 nM
55 nM (CDK2/cyclin E)

NG-57

400 nM

NG-59

800 nM

TABLE 1-continued

Exemplary Purine Analogs

| Structure | Code Name | IC$_{50}$ cdc2/cyclin B (additional kinases) |
|---|---|---|
| 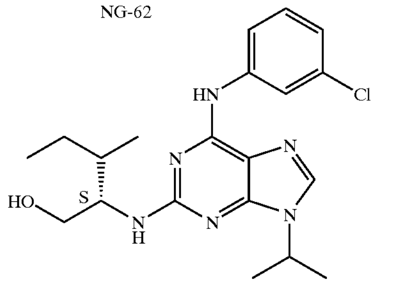 | NG-62 | 500 nM |
| 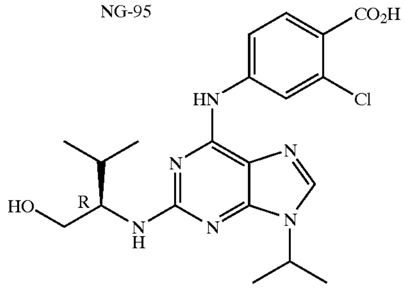 | NG-95 | approx. 20 nM |
| 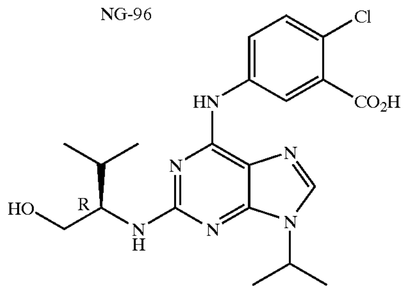 | NG-96 | approx. 30 nM |
| 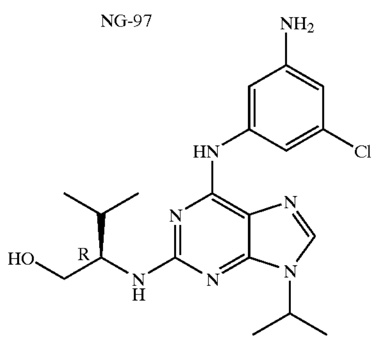 | NG-97 | 30 nM |
| 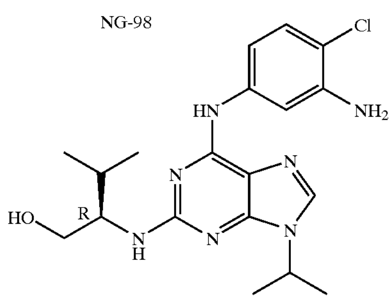 | NG-98 | 30 nM |

TABLE 1-continued

Exemplary Purine Analogs

| Structure | Code Name | IC$_{50}$ cdc2/cyclin B (additional kinases) |
|---|---|---|
| 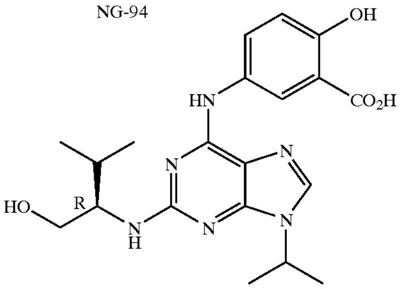 | NG-94 | approx. 100 nM |
| 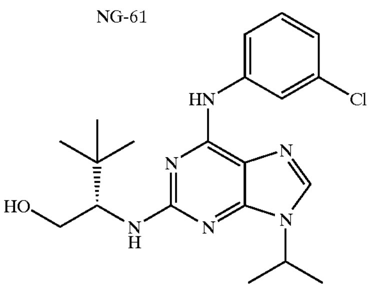 | NG-61 | 2300 nM |

Figure 2:
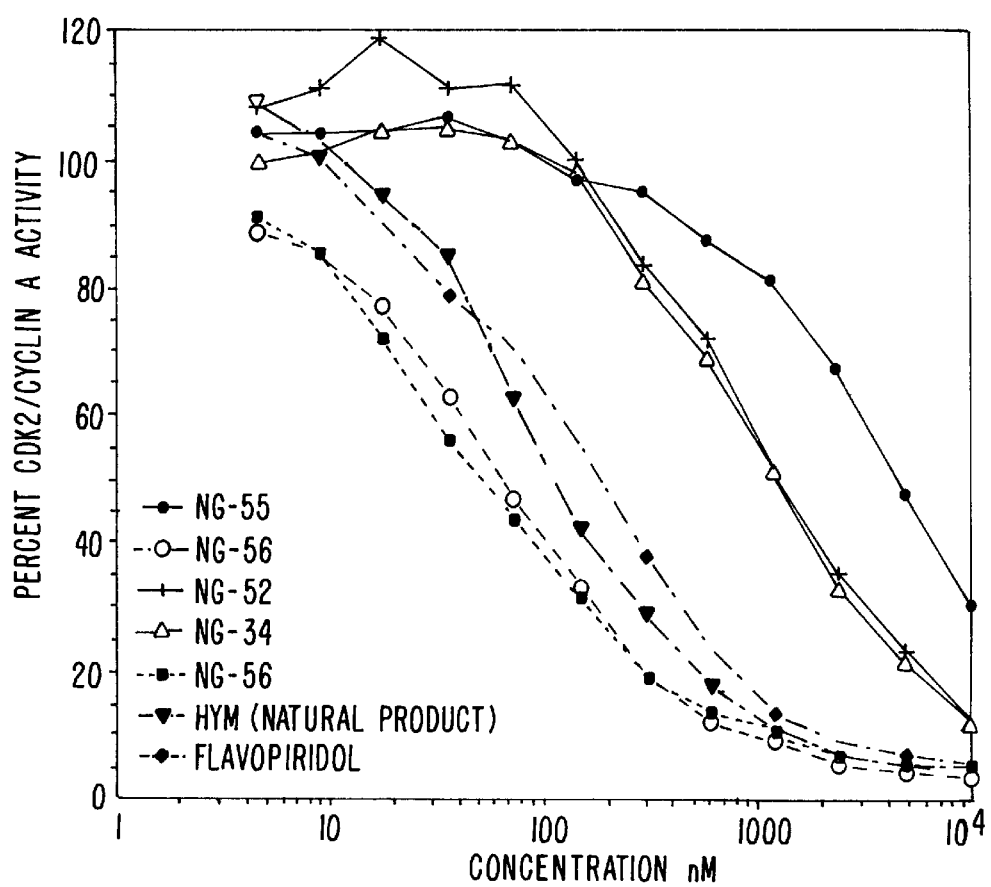
FIGS. 2 and 3 illustrate the $IC_{50}$ for representative compounds from Table 1.
Figure 3:
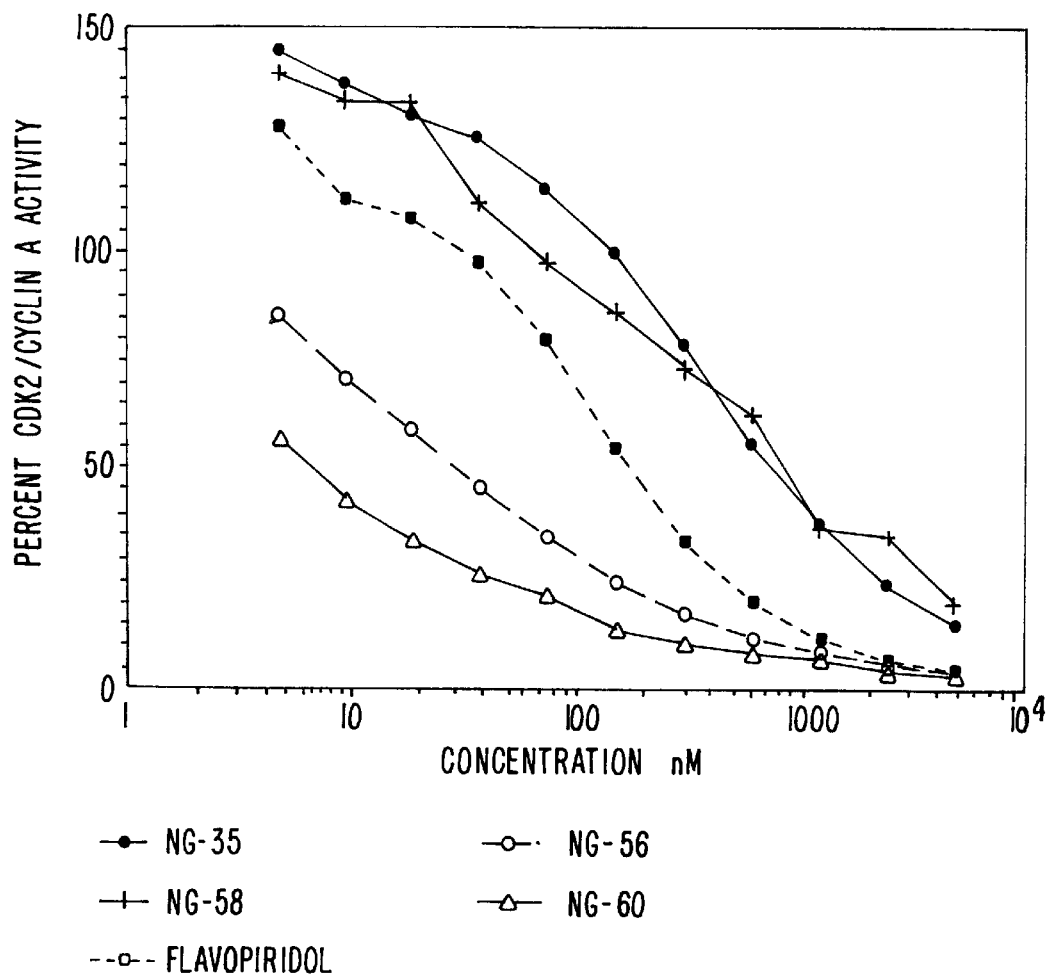

[a]These IC$_{50}$s can be compared with other known small molecule inhibitors of CDK2 (see, FIGS. 2 and 3).

It will be readily appreciated by those of skill in the art that depending on the substituents, the purine analogs of the present invention can be a racemic mixture or either of a pair of diastereomers or enantiomers.

The purine analogs of the present invention can be synthesized in a variety of ways, using conventional synthetic chemistry techniques. Typically, the compounds of the present invention are prepared according to Scheme I, wherein $R^1$, $R^2$, $R^3$ $R^4$, and $R^5$ are as defined above. The use of appropriate organic solvents, temperature and time conditions for running the reactions are within the level of skill in the art. Reactions of this type are generally described by Norman, et al., *J. Am. Chem. Soc.* 118:7430–7431 (1996); and Gray, et al., *Tetrahedron Letters* 38:1161–1164 (1997), the teachings of which are incorporated herein by reference. Moreover, suitable synthesis reactions are illustrated herein by the representative examples. Necessary starting materials can be obtained by standard procedures of organic chemistry.

SCHEME 1

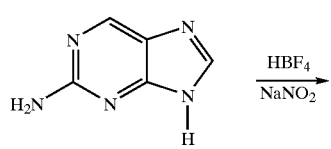

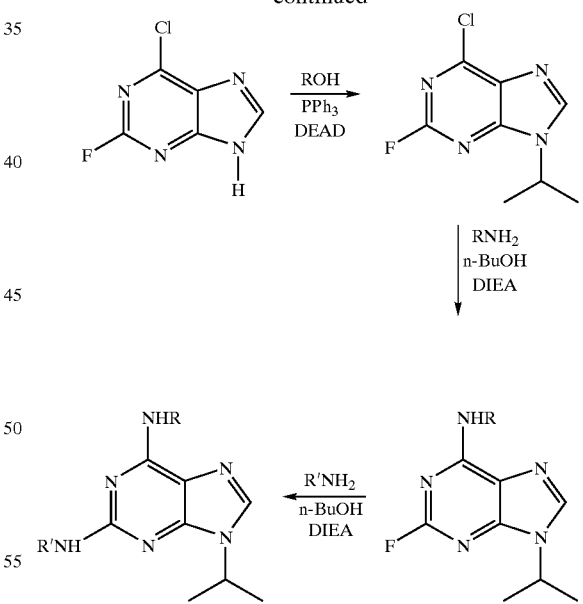

Briefly, as illustrated in Scheme I, a purine derivative with a halogen at the 2-position is alkylated at the 9-position with an alcohol using the Mitsonubo alkylation. Following the alkylation, the purine derivative is aminated at the 6-position with an amine. Once prepared, the purine analogs can be purified (e.g., by TLC), characterized (e.g., by Reverse Phase HPLC) and analyzed (e.g., by high resolution spectroscopy using, for example, $^1$H NMR or FAB-MS).

COMBINATORIAL LIBRARIES OF PURINE ANALOGS

To rapidly examine the effects of substituents on the purine ring, combinatorial chemical libraries of purine analogs are synthesized in which the 2, 6 and 9 positions are varied. A combinatorial chemical library is a collection of diverse chemical compounds generated by combining a number of chemical "building blocks" such as reagents. The "building blocks" can be combined either through chemical or biological synthesis. For example, a linear combinatorial chemical library such as an oligonucleotide library is formed by combining a set of chemical building blocks called nucleotides in every possible way for a given compound length (i.e., the number of nucleotides in a nucleic acid compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, (1991) *Int. J. Pept. Prot. Res.* 37: 487–493, Houghton, et al. (1991) *Nature* 354: 84–88). Peptide synthesis is by no means the only approach envisioned. Other chemistries for generating chemical diversity libraries can also be used. Such chemistries include, but are not limited to; peptoids (PCT Publication No. WO 91/19735, Dec. 26, 1991), encoded peptides (PCT Publication WO 93/20242, Oct. 14, 1993), random bio-oligomers (PCT Publication WO 92/00091, Jan. 9, 1992), benzodiazepines (U.S. Pat. No. 5,288,514), diversomers such as hydantoins, benzodiazepines and dipeptides (Hobbs, et al. (1993) *Proc. Nat'l Acad. Sci. USA* 90: 6909–6913), vinylogous polypeptides (Hagihara, et al. (1992) *J. Amer. Chem. Soc.* 114: 6568), nonpeptidal peptidomimetics with a β-D-Glucose scaffolding (Hirschmann, et al., (1992) *J. Amer. Chem. Soc.* 114: 9217–9218), analogous organic syntheses of small compound libraries (Chem, et al. (1994) *J. Amer. Chem. Soc.* 116: 2661), oligocarbamates (Cho, et al., (1993) *Science* 261:1303), and/or peptidyl phosphonates (Campbell, et al., (1994) *J. Org. Chem.* 59: 658; Gordon, et al., (1994) *J. Med. Chem.* 37: 1385), nucleic acid libraries (see, e.g., Strategene, Corp.), peptide nucleic acid libraries (see, e.g., U.S. Pat. No. 5,539,083) antibody libraries (see, e.g., Vaughn, et al. (1996) *Nature Biotechnology* 14(3): 309–314), and PCT/US96/10287), carbohydrate libraries (see, e.g., Liang, et al. (1996) *Science* 274:1520–1522, and U.S. Pat. No. 5,593,853), and small organic molecule libraries (see, e.g., benzodiazepines: Baum (1993) C&EN, January 18, page 33; isoprenoids: U.S. Pat. No. 5,569,588; thiazolidinones and metathiazanones: U.S. Pat. No. 5,549,974; pyrrolidines: U.S. Pat. Nos. 5,525,735 and 5,519,134; morpholino compounds: U.S. Pat. No. 5,506,337; benzodiazepines: 5,288,514; and the like).

Devices for the preparation of combinatorial libraries are commercially available (see, e.g., 357 MPS, 390 NWS, Advanced Chem Tech, Louisville Ky.; Symphony, Rainin, Woburn, Mass., 433A Applied Biosystems, Foster City, Calif.; 9050 Plus, Millipore, Bedford, Mass.).

A number of well known robotic systems have also been developed for solution phase chemistries. These systems include automated workstations like the automated synthesis apparatus developed by Takeda Chemical Industries, LTD. (Osaka, Japan) and many robotic systems utilizing robotic arms (Zymate 11, Zymark Corporation, Hopkinton, Mass.; Orca, Hewlett-Packard, Palo Alto, Calif.) which mimic the manual synthetic operations performed by a chemist. Any of the above devices are suitable for use with the present invention. The nature and implementation of modifications to these devices (if any) so that they can operate as discussed herein will be apparent to persons skilled in the relevant art. In addition, numerous combinatorial libraries are themselves commercially available (see, e.g., ComGenex, Princeton, N.J., Asinex, Moscow, Russia, Tfipos, Inc., St. Louis, Mo., ChemStar, Ltd, Moscow, Russia, 3D Pharmaceuticals, Exton, Pa., Martek Biosciences, Columbia, Md., etc.).

Figure 4A:
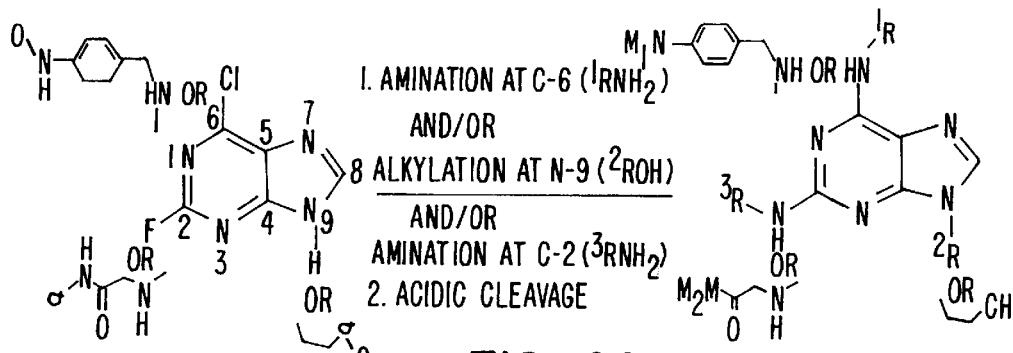
FIG. 4A provides a scheme for the combinatorial synthesis of 2,6,9-trisubstituted purines from a 2, 6, or 9 linked purine scaffold using amination and alkylation chemistries. Chemical structures of CDK inhibitors.

In the instant invention, a typical starting point is a 2-fluoro-6-chloropurine framework (FIG. 4A). Substitution chemistry is then used to install amines or other functional groups at the 2- and 6-positions and, in a preferred embodiment, a Mitsunobu reaction is employed to alkylate the N-9 position of the purine core. See, Mitsonobu, *Synthesis* 1–28 (1981); and Toyota, et al., *Heterocycles* 36:1625–1630 (1993). This type of substitution chemistry allows introduction of a wide range of primary and secondary functional groups, while the Mitsunobu reaction tolerates primary and secondary alcohols lacking additional acidic hydrogens. Newly appended groups are then modified combinatorially in subsequent steps using a variety of chemistries including acylation, reductive amination, and Suzuki coupling reactions (Backes, et al., *J. Am. Chem. Soc.* 116:11171–11172 (1994)). In preferred embodiments of the instant invention, for library synthesis, one position of the purine ring is held invariant to allow attachment to a solid support. Libraries are then synthesized in a spatially-separated format using either a pin apparatus (Geysen, et al., *Immunol. Methods* 102:(1987) or a polystyrene resin, and then screened for activity.

PURINE ANALOG ACTIVITY ASSAYS

After a purine library has been created, the compounds are screened for kinase inhibitory activity. The most basic type of screen for inhibition of activity is to assay for binding to the target compound, in the instant invention, protein kinases. From the ability to bind to the target, one can predict whether the compound being assayed will inhibit the kinase by competing for the enzyme's natural substrate. However, this type of assay is not fool-proof and some measure of functional activity is desired.

Purine analogs suitable for use in the methods of the present invention can readily be identified using in vitro and in vivo activity screening assays. Such assays may screen for the ability of a particular compound to inhibit malignant tumor cell growth or to abolish tumorigenicity of malignant cells in vitro or in vivo. For instance, tumor cell lines can be exposed to varying concentrations of a purine analog of interest, and the viability of the cells can be measured at set time points using the Alamar Blue™ assay (commercially available from BioSource, International of Camarillo, Calif.). When Alamar Blue™ dye is added to the culture medium, the dye is reduced by cellular mitochondrial enzymes and yields a soluble product with substantially enhanced fluorescence. This fluorescence is then measured with a fluorimeter, whereby the signal is directly proportional to the cell number. Using this information, $IC_{50}$ values[1] for the compounds of interest can be readily be calculated.

[1]$IC_{50}$ is the concentration of compound lethal to 50% of a cell culture as compared to a control culture.

As will be appreciated by the skilled artisan, many varieties of malignant tumor cell cultures and cell lines can be used to screen for activity, including but not limited to, MDA MB 231 (breast), MCF-7 (breast), MDA MB 468 (breast), Siha (squamous cell carcinoma), A549 (non-small cell lung), HL-60 (leukemia) Ovcar-3 (ovarian), etc. In addition, the purine analogs of the present invention can be screened on the National Cancer Institute panel of 60 human tumor cell lines (see, Appendix I). Of course, other in vitro and/or in vivo assays to screen for anti-tumor and/or anti-cancer activity known to and used by the skilled artisan can also be employed to identify effective purine analogs useful in the methods of the present invention.

In a more direct activity assay, the effect on mRNA transcription in the presence of the compounds of this invention is measured. In one embodiment of the invention, the compounds are added to cells in culture. After an incubation for a suitable time, the cells are solubilized in a chaotropic agent, such as guanidine hydrochloride (see, Sambrook, et al. *Molecular Cloning : A Laboratory Manual* (*2nd Ed.*), Vols. 1–3, Cold Spring Harbor Laboratory, (1989) ("Samnbrook") or *Current Protocols In Molecular Biology*, F. Ausubel, et al., ed. Greene Publishing and Wiley-Interscience, New York (1987) ("Ausubel"). The mRNA is then isolated by techniques well known in the art (see, Sambrook, supra) and quantified. Quantification of mRNA can be done by agarose gel electrophoresis, U.V. absorption, northern blotting, and other techniques that are standard in the field of molecular biology.

Alternatively, oligonucleotides present in the mRNA of a cell are screened for hybridization with oligonucleotides provided in a solid phase array. This technique provides the artisan with known oligonucleotides which represent known mRNA.

OLIGONUCLEOTIDE ARRAYS

The present invention provides methods and apparatus for the preparation and use of a substrate having a plurality of polymer sequences in predefined regions. These polymer sequences are then used as a screen for purine analog activity. The invention is described herein primarily with regard to the preparation of molecules containing sequences of nucleotides, but could readily be applied in the preparation of other polymers. Such polymers include, for example, both linear and cyclic polymers of nucleic acids, polysaccharides, phospholipids, and peptides, heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent upon review of this disclosure. In a preferred embodiment, the invention herein is used in the screening of *Saccharomyces cerevesiae* cRNA binding.

The invention preferably provides for the use of a substrate "S" with a surface. Linker molecules "L" are optionally provided on a surface of the substrate. The purpose of the linker molecules, in some embodiments, is to facilitate receptor recognition of the synthesized polymers.

Optionally, the linker molecules may be chemically protected for storage purposes. A chemical storage protective group such as t-BOC (t-butoxycarbonyl) may be used in some embodiments, particularly when assembling peptides on the substrate. Such chemical protective groups would be chemically removed upon exposure to, for example, acidic solution and would serve to protect the surface during storage and be removed prior to polymer preparation.

On the substrate or a distal end of the linker molecules, a functional group with a protective group $P_0$ is provided. The protective group $P_0$ may be removed upon exposure to radiation, electric fields, electric currents, or other activators to expose the functional group.

In a preferred embodiment, the radiation is ultraviolet (UV), infrared (IR), or visible light. As is more fully described in U.S. Pat. No. 5,512,270, which in incorporated by reference in its entirety, the protective group may alternatively be an electrochemically-sensitive group which may be removed in the presence of an electric field. In still further alternative embodiments, ion beams, electron beams, or the like may be used for deprotection.

In some embodiments, the exposed regions and, therefore, the area upon which each distinct polymer sequence is synthesized are smaller than about 1 $cm^2$ or less than 1 $mm^2$. In preferred embodiments the exposed area is less than about 10,000 $\mu m^2$ or, more preferably, less than 100 $\mu m^2$ and may, in some embodiments, encompass the binding site for as few as a single molecule. Within these regions, each polymer is preferably synthesized in a substantially pure form.

Concurrently, or after exposure of a known region of the substrate to light, the surface is contacted with a first monomer unit $M_1$ which reacts with the functional group which has been exposed by the deprotection step. The first monomer includes a protective group $P_1$. $P_1$ may or may not be the same as $P_0$.

Accordingly, after a first cycle, known first regions of the surface may comprise the sequence:

S-L-$M_1$-$P_1$ while remaining regions of the surface comprise the sequence:

S-L-$P_0$.

Thereafter, second regions of the surface (which may include the first region) are exposed to light and contacted with a second monomer $M_2$ (which may or may not be the same as $M_1$) having a protective group $P_2$. $P_2$ may or may not be the same as $P_0$ and $P_1$. After this second cycle, different regions of the substrate may comprise one or more of the following sequences:

S-L-$M_1$-$M_2$-$P_2$
S-L-$M_2$-$P_2$
S-L-$M_1$-$P_1$ and/or
S-L-$P_0$.

The above process is repeated until the substrate includes desired polymers of desired lengths. By controlling the locations of the substrate exposed to light and the reagents exposed to the substrate following exposure, the location of each sequence will be known.

Thereafter, the protective groups are removed from some or all of the substrate and the sequences are, optionally, capped with a capping unit C. The process results in a substrate having a surface with a plurality of polymers of the following general formula:

$$S-[L]-(M_i)-(M_j)-(M_k)\ldots(M_x)-[C]$$

where square brackets indicate optional groups, and $M_i \ldots M_x$ indicates any sequence of monomers. The number of monomers could cover a wide variety of values, but in a preferred embodiment they will range from 2 to 100.

In some embodiments a plurality of locations on the substrate polymers contain a common monomer subsequence. For example, it may be desired to synthesize a sequence $S-M_1-M_2-M_3$ at first locations and a sequence $S-M_4-M_2-M_3$ at second locations. The process would commence with irradiation of the first locations followed by contacting with $M_1$-P, resulting in the sequence $S-M_1$-P at the first location. The second locations would then be irradiated and contacted with $M_4$-P, resulting in the sequence $S-M_4$-P at the second locations. Thereafter both the first and second locations would be irradiated and contacted with the dimer $M_2-M_3$, resulting in the sequence $S-M_1-M_2-M_3$ at the first locations and $S-M_4-M_2-M_3$ at the second locations. Of course, common subsequences of any length could be utilized including those in a range of 2 or more monomers, 2 to 100 monomers, 2 to 20 monomers, and a most preferred range of 2 to 3 monomers.

According to other embodiments, a set of masks is used for the first monomer layer and, thereafter, varied light wavelengths are used for selective deprotection. For example, in the process discussed above, first regions are first exposed through a mask and reacted with a first monomer having a first protective group $P_1$, which is removable upon exposure to a first wavelength of light (e.g., IR). Second regions are masked and reacted with a second monomer having a second protective group $P_2$, which is removable upon exposure to a second wavelength of light (e.g., UV). Thereafter, masks become unnecessary in the synthesis because the entire substrate may be exposed alternatively to the first and second wavelengths of light in the deprotection cycle. For a more complete description of masking technologies, see U.S. Pat. No. 5,445,934, which is incorporated by reference in its entirety.

The polymers prepared on a substrate according to the above methods will have a variety of uses including, for example, screening for biological activity. In such screening activities, the substrate containing the sequences is exposed to an unlabeled or labeled drug, oligonucleotide, including mRNA or cRNA, receptor such as an antibody, receptor on a cell, phospholipid vesicle, and/or any one of a variety of other receptors.

In a preferred embodiment, the hybridization under stringent conditions of nucleic acid, such as mRNA or cRNA to oligonucleotides on the surface of the array is desired. Hybridization under stringent conditions is defined as maintaining hybridization in 0.2×SSC at 65° C. for 15 minutes. See, Sambrook for a description of SSC buffer. After the nucleic acids have hybridized to the oligonucleotides on the array, the positions of the hybridized nucleic acids is determined. This can be done by a variety of techniques well known to one of skill, but in a preferred embodiment is through biotin labeling of the nucleic acid. From the location of the bound nucleic acid, the identity of the oligonucleotide is discovered and thus the identity of the nucleic acid hybridized to the oligonucleotide.

The receptor molecules, including drugs or oligonucleotides, may bind with one or more polymers on the substrate. The presence of the labeled receptor and, therefore, the presence of a sequence which binds with the receptor is detected in a preferred embodiment through the use of autoradiography, detection of fluorescence with a charge-coupled device, fluorescence microscopy, or the like. The sequence of the polymer at the locations where the receptor binding is detected may be used to determine all or part of a sequence which is complementary to the receptor.

USES OF PURINE ANALOGS OF THIS INVENTION

The compounds of the present invention are useful for treating a wide variety of cancers. Such cancers include, by way of example and not limitation, carcinomas such as pharynx, colon, rectal, pancreatic, stomach, liver, lung, breast, skin, prostate, ovary, cervical, uterine and bladder cancers; leukemias; lymphomas; gliomas; retinoblastomas; and sarcomas. Moreover, in accordance with the above method, mammalian subjects include, but are not limited to, humans, laboratory animals, domestic pets and farm animals.

In another preferred embodiment, the purine analogs of the present invention are used to treat a neurodegenerative disease, the method comprising administering to a mammal having such a disease, a therapeutically effective amount of a compound having the general formula:

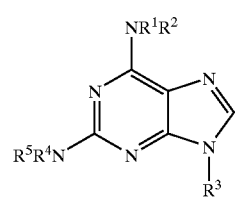

I or a pharmaceutically acceptable salt thereof. The prior discussions pertaining to $R^1$, $R^2$, $R^4$, $R^5$ and $R^6$, their definitions and preferred embodiments are fully applicable to the purine analogs used in this method and, thus, will not be repeated.

Neurodegenerative diseases which can be treated using the purine analog compounds of the present invention include, but are not limited to, neurodegenerative pathologies involving multiple neuronal systems and/or brainstem including Alzheimer's disease, AIDS-related dementia, Leigh's disease, diffuse Lewy body disease, epilepsy, multiple system atrophy, Guillain-Barre syndrome, lysosomal storage disorders such as lipofuscinosis, late-degenerative stages of Down's syndrome, Alper's disease, vertigo as result of CNS degeneration, etc. Other neurodegenerative diseases which can be treated using the purine analogs of the present invention will be readily apparent to those of skill in the art.

In addition, in view of their cell-cycle arresting activities, the purine analogs of the present invention can be used to inhibit undesirable proliferation, including, as described above, cancer, psoriasis, growth of fungi, parasites, viruses, plants, etc. Moreover, the purine analogs of the present invention have apoptosis-inducing effects in actively dividing cells and, thus, can be advantageously used to treat various disease states associated with undesirable proliferation. Such uses are described, for example, in Meijer, L., *Trends in Cell Biology* (1986) 6:393–397, the teachings of which are incorporated herein by reference for all purposes.

In addition to the foregoing, the purine analogs of the present invention can be used in vitro as molecular tools and probes. For instance, since CDK inhibitors arrest cells both in $G_1$ and late $G_2$/early prophase, they can be used to synchronize cells when used preferably in combination with another synchronizing agent/method (e.g., when used in combination with aphidicolin). In addition, immobilized CDK inhibitors can be used for affinity purification/depletion of CDKs from cellular extracts. Such purine analogs will be particularly useful for massive purification of expressed CDKs (for crystallography or screening purposes). In addition, such purine analogs are useful for comparative analysis of CDKs extracted from cells at difference developmental or cell-cycle stages (variation of concentration, kinase activity, post-translational modifications, etc.).

PHARMIACEUTICAL FORMULATIONS/ ROUTES OF ADMINISTRATION

After the screening methods described above have identified purine analogs that inhibit CDKs, the compounds, i.e., purine analogs, of the present invention can be administered to a mammal, e.g., a human patient, alone, in the form of a pharmaceutically acceptable salt, or in the form of a pharmaceutical composition where the compound is mixed with suitable carriers or excipient(s) in a therapeutically effective amount, e.g., at doses effective to inhibit a protein kinase or a cellular process or achieve amelioration of symptoms of a disease associated with a protein kinase.

The compounds of this invention can be incorporated into a variety of formulations for therapeutic administration. More particularly, the compounds of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, pills, powders, granules, dragees, gels, slurries, ointments, solutions, suppositories, injections, inhalants and aerosols. As such, administration of the compounds can be achieved in various ways, including oral, buccal, rectal, parenteral, intraperitoneal, intradermal, transdermal, intracheal, etc., administration. Moreover, the compound can be administered in a local rather than systemic manner, for example via injection of the compound directly into a solid tumor, often in a depot or sustained release formulation. In addition, the compounds can be administered in a targeted drug delivery system, for example, in a liposome coated with tumor-specific antibody. Such liposomes will be targeted to and taken up selectively by the tumor.

The purine analogs of the present invention can be administered alone, in combination with each other, or they can be used in combination with other known compounds (e.g., other drugs, such as anti-cancer drugs, anti-mitotics, anti-inflammatories, antibiotics, corticosteroids, vitamins, etc.). More particularly, the compound of the present invention can be used in conjunctive therapy with other known chemotherapeutic or antineoplastic agents (e.g., vinca alkaloids, antibiotics, antimetabolites, platinum coordination complexes, etc.). For instance, the compounds of the present invention can be used in conjunctive therapy with a vinca alkaloid compound, such as vinblastine, vincristine, taxol, etc.; an antibiotic, such as adriamycin (doxorubicin), dactinomycin (actinomycin D), daunorubicin (daunomycin, rubidomycin), bleomycin, plicamycin (mithramycin) and mitomycin (mitomycin C), etc.; an antimetabolite, such as methotrexate, cytarabine (AraC), azauridine, azaribine, fluorodeoxyunridine, deoxycoformycin, mercaptopurine, etc.; or a platinum coordination complex, such as cisplatin (cis-DDP), carboplatin, etc. In addition, those of skill in the art will appreciate that the compounds of the present invention can be used in conjunctive therapy with other known chemotherapeutic or antineoplastic compounds. In pharmaceutical dosage forms, the compounds may be administered in the form of their pharmaceutically acceptable salts, or they may also be used alone or in appropriate association, as well as in combination with other pharmaceutically active compounds.

Suitable formulations for use in the present invention are found in *Remington's Pharmaceutical Sciences* (Mack Publishing Company, Philadelphia, Pa., 17th ed. (1985)), which is incorporated herein by reference. Moreover, for a brief review of methods for drug delivery, see, Langer, *Science* 249:1527–1533 (1990), which is also incorporated herein by reference. The pharmaceutical compositions described herein can be manufactured in a manner that is known to those of skill in the art, e.g., by means of conventional mixing, dissolving, granulating, dragee-making, levigating, emulsifying, encapsulating, entrapping or lyophilizing processes. The following methods and excipients are merely exemplary and are in no way limiting.

For injection, the compounds can be formulated into preparations by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, the compounds of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter, carbowaxes, polyethylene glycols or other glycerides, all of which melt at body temperature, yet are solid at room temperature.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art. Sustained-release capsules may, depending on their chemical nature, release the compounds for a few weeks up to over 100 days.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Pharmaceutical compositions suitable for use in the present invention include compositions wherein the active ingredients are contained in a therapeutically effective amount. The amount of composition administered will, of course, be dependent on the subject being treated, on the subject's weight, the severity of the affliction, the manner of administration and the judgment of the prescribing physician. Determination of an effective amount is well within the capability of those skilled in the art, especially in light of the detailed disclosure provided herein.

For any compound used in the method of the invention, a therapeutically effective dose can be estimated initially from cell culture assays. For example, a dose can be formulated in animal models to achieve a circulating concentration range that includes the $IC_{50}$ as determined in cell culture, or the $IC_{100}$ as determined in cell culture (i.e., the concentration of compound that is lethal to 100% of a cell culture). Such information can be used to more accurately determine useful doses in humans. Initial dosages can also be estimated from in vitro or in vivo data.

Initial dosages can also be formulated by comparing the effectiveness of the compounds described herein in cell culture assays with the effectiveness of known drugs. For instance, when used as anticancer agents, initial dosages can be formulated by comparing the effectiveness of the compounds described herein in cell culture assays with the effectiveness of known anti-cancer drugs such as vincristine. In this method, an initial dosage can be obtained by multiplying the ratio of effective concentrations obtained in cell culture assay for the a compound of the present invention and a known anti-cancer drug by the effective dosage of the known anti-cancer drug. For example, if a compound of the present invention is twice as effective in cell culture assay than vincristine (i.e., the $IC_{50}$ of that compound is equal to one-half the $IC_{50}$ of vincristine in the same assay), an initial effective dosage of the compound of the present invention would be one-half the known dosage for vincristine. Using these initial guidelines one having ordinary skill in the art can determine an effective dosage in humans.

Moreover, toxicity and therapeutic efficacy of the compounds described herein can be determined by standard pharmaceutical procedures in cell cultures or experimental animals, e.g., by determining the $LD_{50}$, (the dose lethal to 50% of the population) and the $ED_{50}$ (the dose therapeutically effective in 50% of the population). The dose ratio between toxic and therapeutic effect is the therapeutic index and can be expressed as the ratio between $LD_{50}$ and $ED_{50}$. Compounds which exhibit high therapeutic indices are preferred. The data obtained from these cell culture assays and animal studies can be used in formulating a dosage range that is not toxic for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1, p. 1).

Dosage amount and interval may be adjusted individually to provide plasma levels of the active compound which are sufficient to maintain therapeutic effect. Usual patient dosages for oral administration range from about 50–2000 mg/kg/day, commonly from about 100–1000 mg/kg/day, preferably from about 150–700 mg/kg/day and most preferably from about 250–500 mg/kg/day. Preferably, therapeutically effective serum levels will be achieved by administering multiple doses each day. In cases of local administration or selective uptake, the effective local concentration of the drug may not be related to plasma concentration. One having skill in the art will be able to optimize therapeutically effective local dosages without undue experimentation.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example 1

Example 1 illustrates a general synthetic scheme for producing the purine derivatives of the invention on a solid support. The solid-phase synthesis strategy exemplified by Scheme 2 involves attaching the growing compound to the solid-support via the side-chain at position 2 of the purine ring structure.

Scheme 2

Library #1:

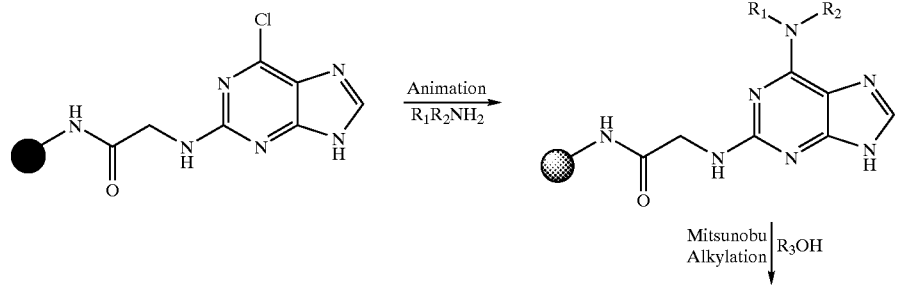

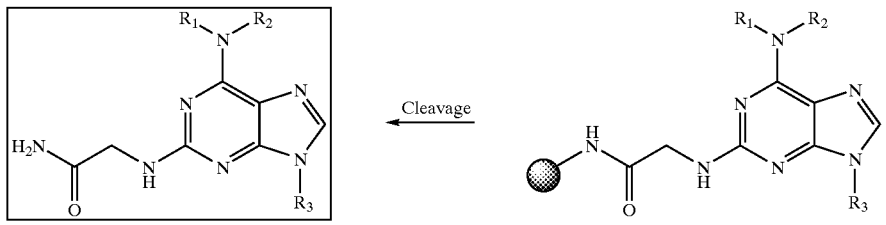

The following examples illustrate both general and specific methods for synthesizing a wide array of the purine derivatives of the present invention.

Example 2

Example 2 illustrates a generalized synthetic route to purine derivatives on a solid support. The solid-phase synthesis strategy exemplified by Scheme 3 involves attaching the growing compound to the solid-support via the side-chain at position 9 of the purine ring structure.

Scheme 3

Library #2:

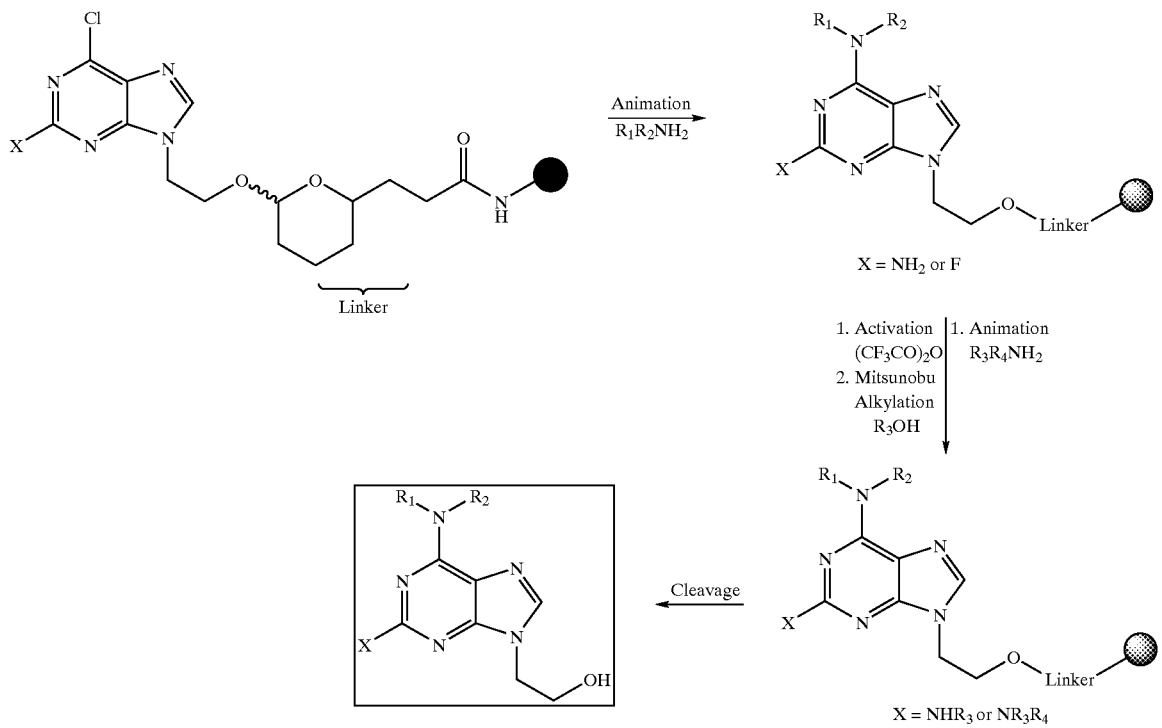

Example 3

Example 3 illustrates a general route to purine derivatives synthesized on a solid support. The route exemplified by Scheme 4 involves attaching the growing compound to the solid-support via the substituent at the 6-position of the purine ring.

Scheme 4

Library #3:

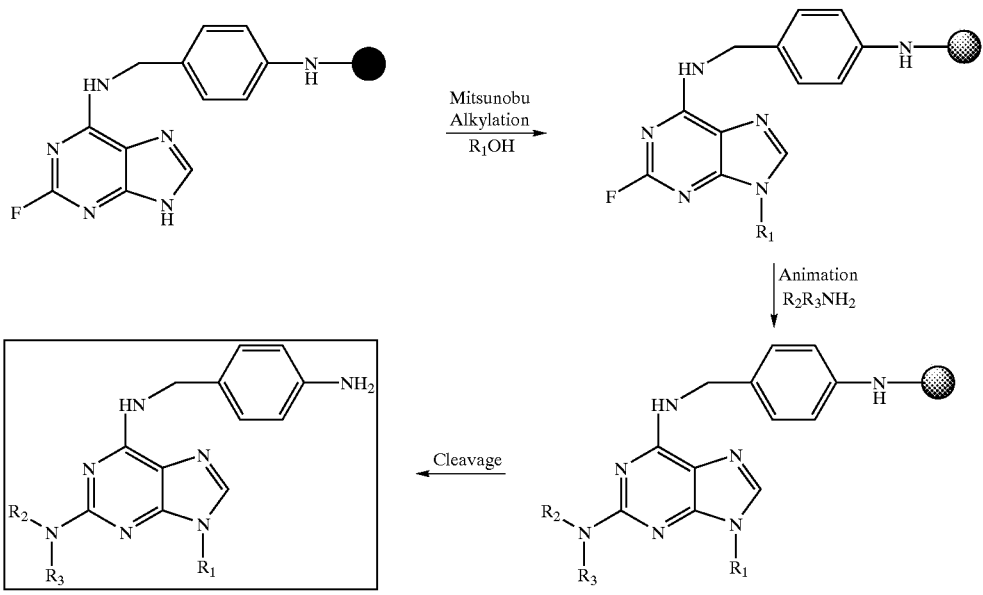

Example 4

Example 4 details the alkylation of position 9 of a purine nucleus. The synthetic route is summarized in Scheme 5.

Scheme 5

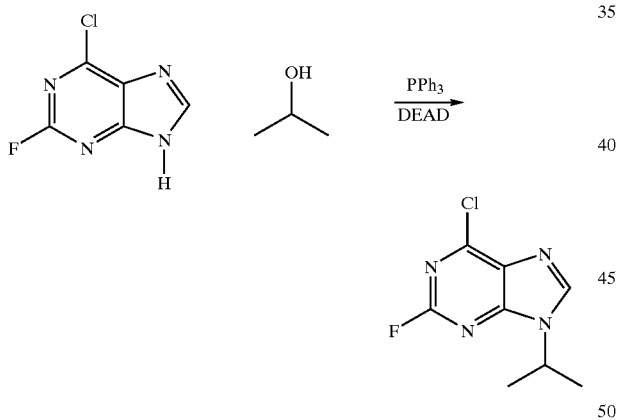

2-Fluoro-6-chloropurine (900 mg 5.20 mmol) and PPh3 (3.0 g, 10.4 mmol) were combined in a flame-dried flask under $N_2$. Freshly distilled THF (60 mL) was added followed by 2-propanol (800 μL, 10.4 mmol). The mixture was cooled to −10° C. in an ethylene glycol/dry ice bath. DEAD (850 μL, 10.4 mmol) was added over 10 min. The mixture was stirred at −10° C. and gradually returned to room temperature over 3 hours.

The reaction was quenched by adding water (500 μL) to the reaction mixture. The solvent was removed in vacuo to yield a viscous yellow oil. The oil was azeotroped with $CH_2Cl_2$ (2×10 mL) to remove trace THF. Purification was effected by column chromatography on silica gel eluted with $CH_2Cl_2$. The $CH_2Cl_2$ was removed from the desired fraction. The desired product was isolated in 57% yield as a white powder.

Example 5

Example 5 illustrates the synthetic route to amination of the 6-position of the purine ring system. The synthetic route is illustrated in Scheme 6.

Scheme 6

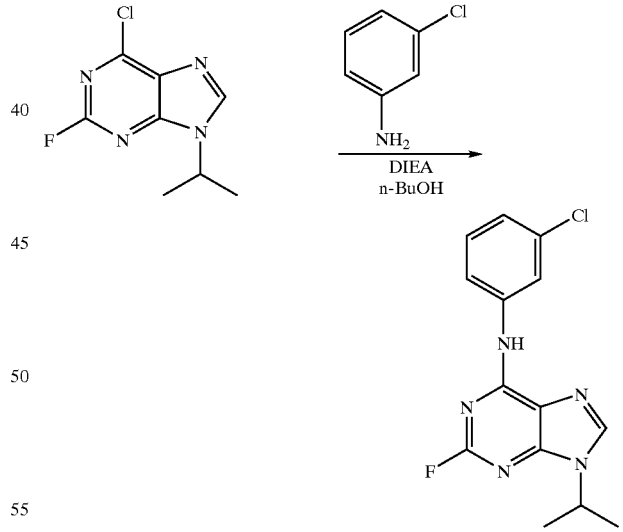

The compound from Example 4 (3.75 g, 17.47 mmol) was combined with 3-chloroaniline (1.85 mL, 17.47 mmol) and diisopropylethylamine (3.05 mL, 17.47 mmol) in n-BuOH. The reaction mixture was heated to 70° C.–80° C. for 11 hours. The n-BuOH was removed under vacuum and the resulting residue was suspended in $H_2O$ to produce a slurry. The product was isolated by filtration, washed with small portions of $CH_2Cl_2$ and $Et_2O$. The product was dried first under a stream of air and then under vacuum. The desired product was isolated in 58% yield.

Example 6

Example 6 details the amination of the 2-position of the purine ring system. The synthetic route is illustrated in Scheme 7.

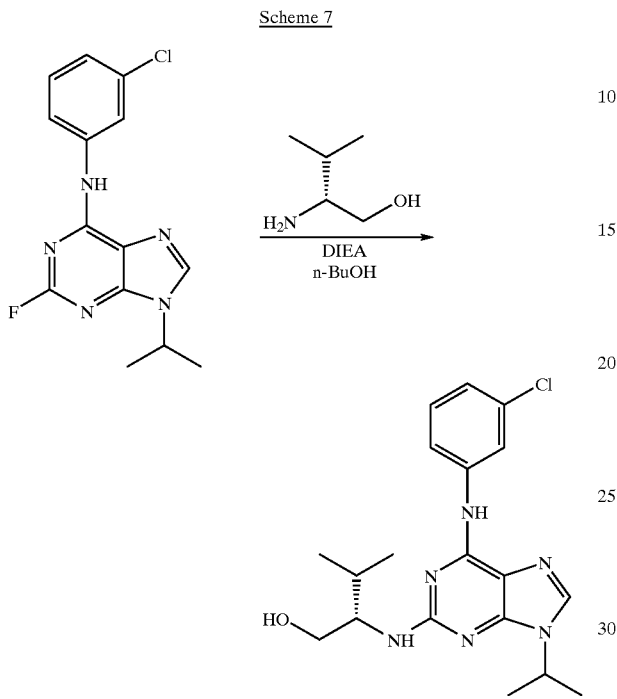

Scheme 7

The compound from Example 5 (1.55 g, 5.10 mmol), 2-amino-3-methyl-1-butanol (559 μL, 5.10 mmol) and diisopropylethylamine (892 μL, 5.10 mmol) were combined in n-BuOH. The mixture was heated to approximately 100° C. The solvent was removed under reduced pressure and the residue purified by silica gel chromatography using 99:1 $CH_2Cl_2$:MeOH to elute. The desired product was isolated in 71% yield.

Example 7

This example illustrates a CDK2/cyclinA microtiter protein kinase assay which can be used to screen the purine analogs of the present invention for inhibitory activity.

1. Required Buffers and Solutions
   a. Buffer A: 80 mM Tris (pH=7.2) mM $MgCl_2$
      Recipe: 4.84 g Tris (F.W.=121.1 g/mol) 4.07 g $MgCl_2$ (F.W.=203.31 g/mol) dissolved in 500 mL of dd$H_2O$. pH adjusted to 7.2 with HCl.
   b. Histone H1 solution: 0.45 mg/ml Histone H1 in 20 mM HEPES pH=7.2.
      Recipe: 5 mg of Histone H1 in 11.111 mL of 20 mM HEPES pH=7.2. 477 m of HEPES provided in 1 mL aliquots. Store at −80° C.
   c. ATP solution: 90 μM ATP, 300 μg/mL BSA, 3 mM DTT.
      Recipe: 9.25 mg DTT, 1.01 mg ATP (F.W.=560 g/mol), 6 mg BSA dissolved in 20 mL dd$H_2O$. provided in 1 mL aliquots. Store at −80° C.
   d. CDK2 solution: 10 mM HEPES pH=7.2,25 mM NaCl, 0.5 mM DTT, 10% glycerol. provided in 192 μL aliquots. Store at −80° C.

2. Stepwise Description of Assay.
   a. Prepare solutions of inhibitors at three times the desired final assay concentration in dd$H_2O$ with 15% DMSO by volume.
   b. Dispense 20 μL of inhibitors to th e well of a microtiter-formatted assay tray.
   c. Thaw Histone H1 solution (1 mL aliquot), ATP solution (1 mL aliquot) and CDK2 solution (192 μL aliquot).
   d. Dilute 192 μL of CDK2 solution into 2.1 mL of buffer A. Swirl to mix. Dispense 20 μL of this solution to each well using a multichannel pipetman. (Note it is important to have a fairly pointed trough for loading the multichannel to avoid running out of solution.)
   e. Mix 1 mL of Histone H1 solution with 1 mL of the ATP solution in a 10 mL screw cap tube. Swirl to mix. Add 2–3 μL of $\gamma$-$^{32}$P-ATP (10 μCi/mL). Mix thoroughly to get even distribution of ATP but be careful to avoid frothing. Dispense to wells with multichannel pipetman; mix the solution in the wells half a dozen times with the multichannel pipetman.
   f. Let reactions proceed for 30 minutes. While reactions are running:
      i) Presoak a 9×12 cm piece of nitrocellulose (0.22 μm) in water for 10 minutes.
      ii) Load the nitrocellulose paper onto the dot blot apparatus. Load 100 μL of water into each well of the dot blot to rehydrate the membrane. Apply a weak vacuum to remove the excess water, but do not dry out the membrane.
      iii) Add 35 μL of 10% TCA to each well of the dot blot.
   g. Using the multichannel pipetman, transfer 35 μL of the reaction mixtures to each well of the dot blot in the same fashion as the ATP was dispensed (to insure equal reaction times).
   h. Add an additional 35 μL of 10% TCA and apply a weak vacuum until the wells are free of liquid. Repeat the process of adding 35 μL of 10% TCA and draining with the vacuum two more times.
   i. Add 35 μL of water to each well of the dot blot and apply a weak vacuum until the wells are free of liquid. Carry out this process a total of four times.
   j. Transfer the nitrocellulose membrane from the dot blot apparatus into a small tray containing enough water to cover the membrane. Let the membrane sit in the water for ten minutes then decant. Wash the membrane in this fashion with three batches of water.
   k. Let the membrane dry completely before analysis with the phosphoimager.

Example 8

Example 8 demonstrates the identification of a CDK2 inhibitor from a purine library.

To rapidly examine the effects of a range of diverse substituents on the purine ring, combinatorial libraries were synthesized in which the 2, 6, and 9 positions were varied starting with a 2-fluoro-6-chloropurine framework (FIG. 4A). See, Gray, et al., *Tetrahedron Lett.* 38, 1161–1164 (1997); and Norman, et al., *J. Am. Chem. Soc.* 118, 7430–7431 (1996). Substitution chemistry was used to install amines at the 2- and 6-positions and a Mitsunobu (Mitsonobu, Synthesis 1–28 (1981) and Toyota, et al., *Heterocycles* 36, 1625–1630 (1993)) reaction was employed to alkylate the N-9 position of the purine core. The substitution chemistry allowed introduction of primary and secondary amines bearing a wide range of functional groups, while the Mitsunobu reaction tolerated primary and secondary alcohols lacking additional acidic hydrogens. Newly appended groups were modified combinatorially in subsequent steps using a variety of chemistries including acylation, reductive amination, and Suzuki coupling reactions (Backes, et al., *J. Am. Chem. Soc.* 116, 11171–11172 (1994)). During library synthesis, one position was held invariant to allow attachment to the solid support. Libraries were synthesized in a spatially-separated format using either a pin apparatus (Geysen, et al., *Immunol. Methods* 102, (1987)) or polystyrene resin and screened for inhibition of Cdk2/cyclinA or Cdc2/cyclinB using a solution phase histone H1 phosphorylation assay.

Inhibitor (20 μL, 15% DMSO in $H_2O$) was introduced to a solution containing CAK activated CDK2/cyclinA (20 μL, 0.3 mg/ml, 80 nM Tris, pH 7.2, 40 mM $MgCl_2$) in a 96-well microtiter array. The kinase reaction was initiated by the addition of substrate histone H1, ATP mixture (20 μL, 0.22 mg/mL histone H1, 10 mM HEPES, pH 7.2, 45 μM ATP, 150 μg/mL BSA, 1.5 mM DTT, 0.1 vol % $\gamma$-$^{32}$P-ATP, 10 μCi/mL). After 30 minutes, the reaction mixtures were transferred to 96-well dot-blot apparatus and quenched by the addition 35 μL of 10% TCA. The phosphorylated histone H1 was immobilized onto a nitrocellulose membrane, washed with 10% TCA followed by $H_2O$ and quantitated by densitometry on a phosphoimager.

In another kinase reaction, starfish cdc2/cyclinB was purified by affinity chromatography as described (Vesely, et al., *Eur. J. Biochem.* 224: 771–786 (199); and Schulze-Gahmen, et al., *Proteins* 22:378–391 (1995)). Kinase assays were performed in the presence of 1 mg/mL hisone H1 (Sigma type III-S), 15 μM $\gamma$-$^{32}$P-ATP (1 mCi/mL), in a final volume of 30 μL. After 10 minutes at 30° C., 25 μL aliquots were spotted onto 2.5×3 cm pieces of phosphocellulose (Whatman P81) and after 20 sec. the filters were washed five times with dilute acid (1 mL phosphoric acid/100 mL $H_2O$). The filters were transferred into 2 mL of ACS (Amersham) scintillation fluid and counted.

By iterating library synthesis and screening, a number of 3- and 4-substituted benzylamines and anilines were identified that led to significant improvements in CDK2 binding when introduced at the 6-position of the purine ring. For example, replacement of the benzylamino group of olomoucine at the C6 position with a 3-chloroaniline resulted in a 10-fold improvement in $IC_{50}$.

Although a variety of hydroxyalkylamino, dihydroxyalkylamino and cycloalkylamino substituents at the 2-position resulted in moderate improvements in binding affinity, much larger increases were achieved using amino alcohols derived from alanine, valine, phenylalanine, and isoleucine. For example, the R-isopropyl side chain of valinol resulted in a 6.5-fold improvement relative to the hydroxyethyl subsituent of olomoucine. These amino alcohols were initially incorporated as racemates but subsequent analysis indicated that the R-stereochemistry resulted in more potent binding. In contrast to many protein kinases that can accommodate larger substituents at the N-9 of the purine ring, CDK2 binding was strongest for those purines bearing small alkyl or hydroxyalkyl substituents.

Following the synthesis and screening of several purine libraries, some compounds as shown in Table 2, in which the 2, 6, and 9-substituents were varied separately, resulted in the most potent CDK2 inhibition. These compounds were used in the synthesis of second generation libraries using solution phase chemistry.

TABLE 2

IC50 values for Purvalanol A and B for a variety of purified kinases.

| Kinase | Purvalanol A ($IC_{50}$ nM) | Purvalanol B ($IC_{50}$ nM) |
| --- | --- | --- |
| cdc2/cyclin B | 40 | 11 |
| cdk2/cyclin A | 70 | 6 |
| cdk2/cyclin E | 35 | 9 |
| cdk4/cyclin D1 | >100 | >10,000 |
| cdk5/p35 | 1,000 | 6 |
| erk1 | 9,000 | 3,333 |
| c-jun-N-terminal kinase | >1,000 | >10,000 |
| protein kinase C α | >10,000 | >100,000 |
| protein kinase C β1 | >10,000 | >100,000 |
| protein kinase C β2 | >10,000 | >100,000 |
| protein kinase C γ | >10,000 | >100,000 |
| protein kinase C δ | >100,000 | >100,000 |
| protein kinase C ε | >100,000 | >100,000 |
| protein kinase C η | >100,000 | >100,000 |
| protein kinase C ζ | >100,000 | >100,000 |
| cAMP-dependent protein kinase | 9,000 | 3,800 |
| cGMP-dependent protein kinase | >10,000 | >100,000 |
| casein kinase 1 | >3,333 | >3,333 |
| GSK3-β | >10,000 | >10,000 |
| insulin-receptor tyrosine kinase | 5,000 | 2,200 |
| casein kinase 2 | >10,000 | >10,000 |
| v-abl | >10,000 | >100,000 |
| cdc28 (*S. cerevisiae*) | 80 | 1,200 |

Figure 4B:
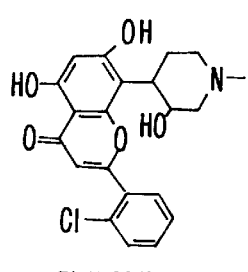
FIG. 4B flavopiridol.
Figure 4C:
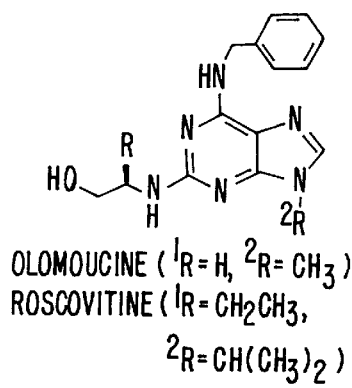
FIG. 4C olomoucine and roscovitine.

$IC_{50}$ data for these series of compounds indicated that the inhibitory effects of these substituents are approximately additive. The most potent inhibitor found was 2-(1R-isopropyl-2-hydroxyethyl)-6-(3-chloroanilino)-9-isopropylpurine (purvalanol A, FIG. 4D) or its water soluble 6-(3-chloro-4-carboxyanilino) analog (purvalanol B, FIG. 4D). These inhibitors have $IC_{50}$'s against CDK2/cyclinA of 70 and 6 nM, respectively. This corresponds to a 1000-fold improvement over olomoucine and a 30-fold improvement over flavopiridol (FIG. 4B), which is among the most potent and selective CDK2 inhibitors known and currently in human clinical trials (Meijer, *Trends in Cell Biol.* 6 (1996)). Both purvalanol A and B showed a high degree of selectivity: among the 22 purified kinases tested (Meijer, et al., *Eur. J. Biochem.* 243:527–536 (1997)) only a subset of the cyclin dependent kinases (Cdc2/cyclin B, CDK2/cyclin A, CDK2/cyclin E) showed potent inhibition (Table 2). In comparison, flavopiridol showed selectivity for CDK1, CDK2, and CDK4, but also inhibited other kinases including PKG at 10-fold higher concentrations.

In order to determine the effects of this CDK directed cell cycle inhibitor on the growth of cells, purvalanol A was tested on the NCI's panel of 60 human tumor cell lines (leukemia, non-small cell lung cancer, colon cancer, renal cancer, prostate cancer, and breast cancer). See Appendix I. The average $GI_{50}$ (50% growth inhibition) of 2 μM is substantially higher than that observed for flavopiridol, which uniformly inhibited cell lines with an average $GI_{50}$ of 72 nM. This result may reflect poorer bioavailability of purvalanol A or the possibility that flavopiridol's mode of action involves inhibition of additional targets. However, two cell lines out of sixty showed an approximately 200-fold greater sensitivity to purvalanol A (KM12 colon cancer cell line with a $GI_{50}$ of 76 nM and the NCI-H522 non-small lung cell line with a $GI_{50}$ of 347 nM), a degree of specificity not observed for growth inhibition by flavopiridol. This selectivity was also evident in the $LC_{50}$ (lethal concentration) experiments in which purvalanol A selectively inhibited colon cancer cell lines at micromolar concentrations.

Example 9

Example 9 details the structural analysis of the CDK2-purvalanol complex.

Figure 5:
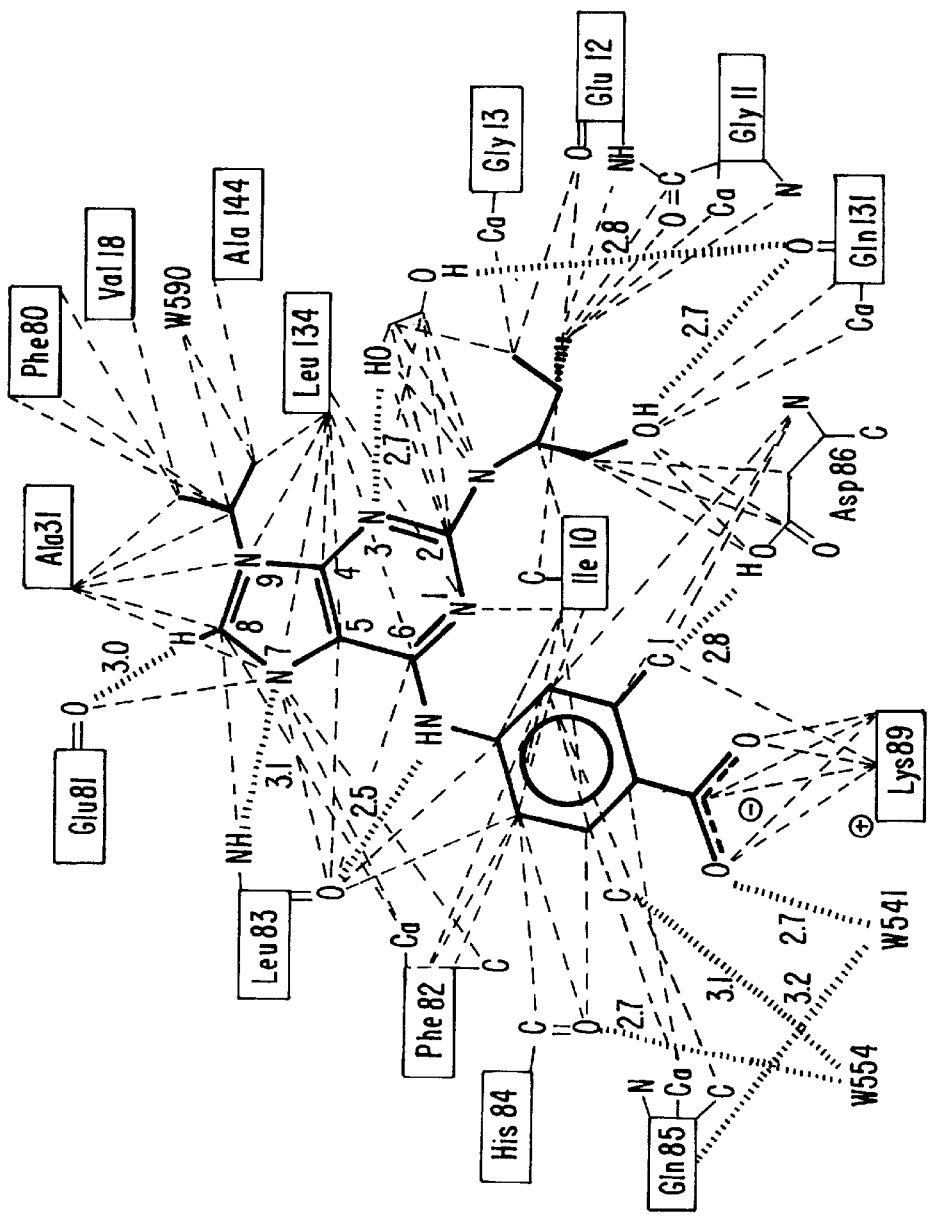
FIG. 5 shows schematic drawing of CDK2 -purvalanol B interactions. Protein side chain contacts are indicated by lines connecting the respective residue box while interactions to main chain atoms are shown as lines to the specific main chain atoms. Van der Waals contacts are indicated by thin dotted lines, and hydrogen bonds by dashed lines. For hydrogen bonds the distances between the non-hydrogen atoms are indicated in angstroms.
Figure 6A:
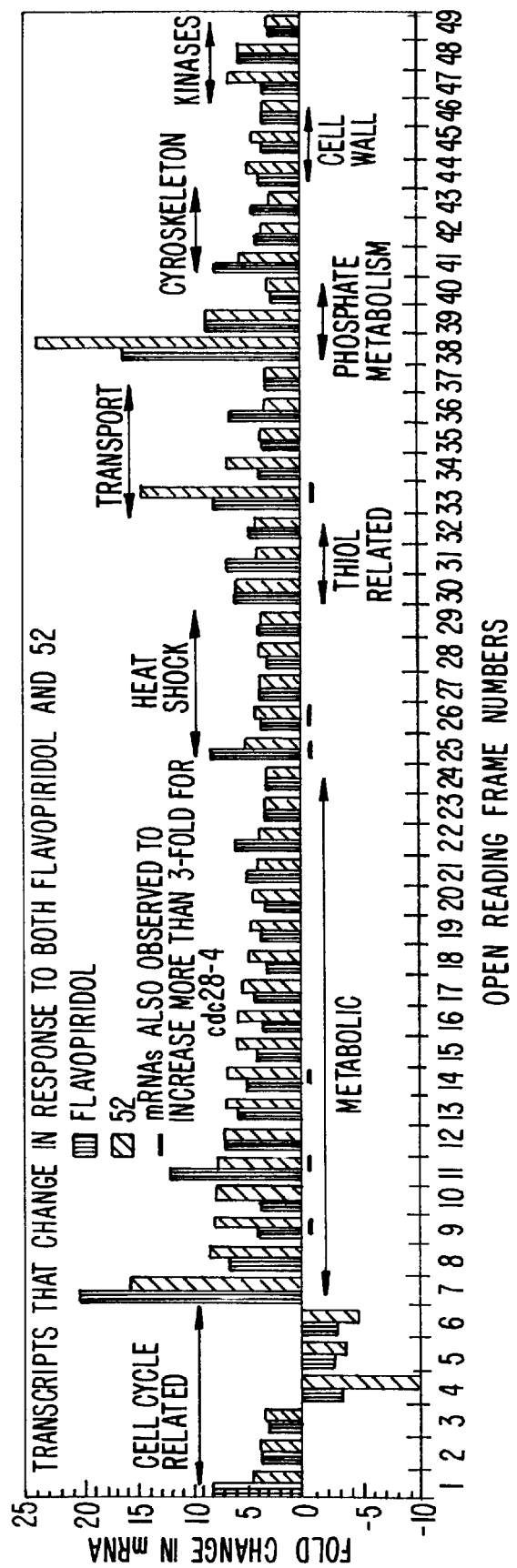
FIG. 6 shows representative transcripts observed to change more than two fold for triplicate hybridizations for each of two independent experiments: (A) names of the genes whose mRNA levels change in common to compound 52 and flavopiridol and (B) transcript changes that may result from Pho85p kinase inhibition observed in either the compound 52 or flavopiridoi profiles; and (C) transcripts that change for cdc28-4, cdc28-4 and compound 52, cdc28-4 and flavopiridol, and compound 52.
Figure 6B:
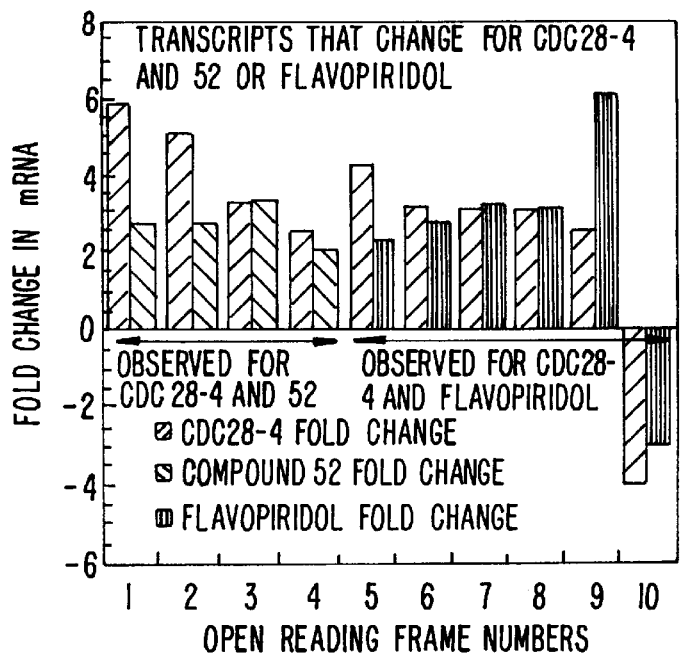
Figure 6C:
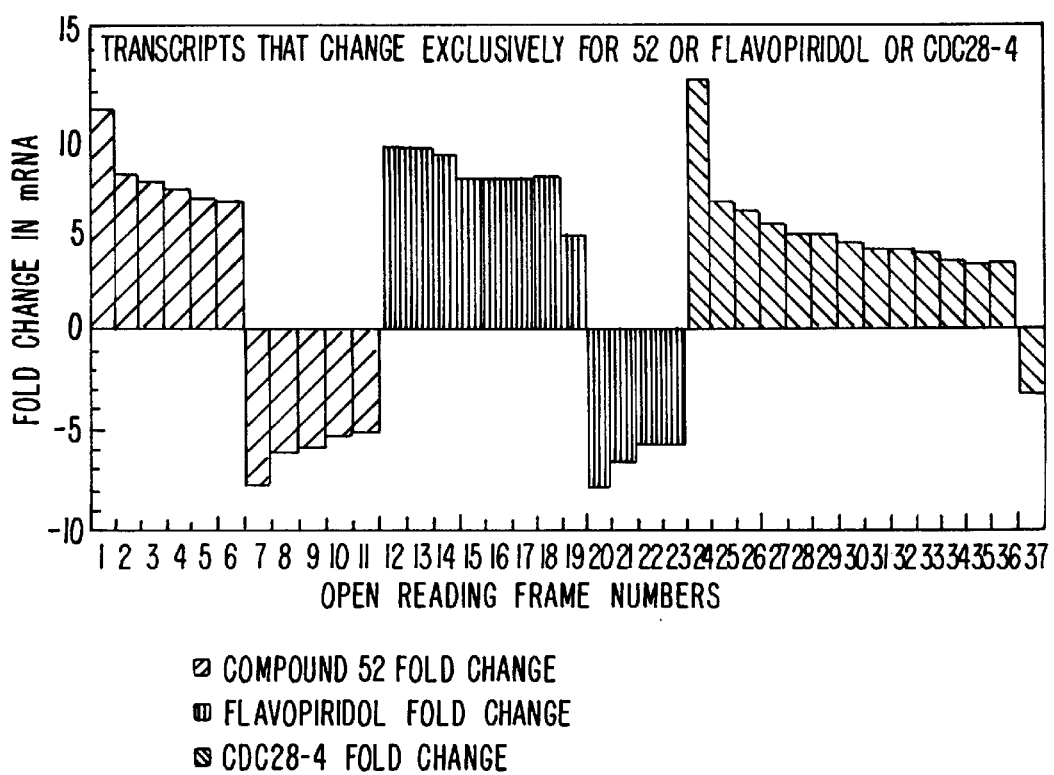

To explore the structural basis for the selectivity and affinity of these inhibitors, the crystal structure of the human CDK2-purvalanol B complex was determined to 2.05 Å resolution and compared to CDK2-ligand complexes containing bound olomoucine (Schulze-Gahmen, et al., *Proteins: Structure, Function, and Genetics*. 22:378–391 (1995)), roscovitine (De Azevedo, et al., *Eur. J. Biochem.* 243:518–526 (1997)), flavopiridol (De Azevedo, et al., *Proc. Nat'l Acad. Sci USA*. 93:2735–2740 (1996)) and ATP (Schultze-Gahmen, et al., *J. Med. Chem* 39:4540–4546 (1996)) (FIG. 5).

Human CDK2 was purified and crystallized as previously described (Rosenblatt, et al, *J. Mol. Biol.* 230:1317 (1993)). Crystals were soaked with purvalanol B in a solution containing 1% DMSO and 5% ethyleneglycol, necessary to solubilize the compound. A procedure involving chemical crosslinking was employed to prevent crystals from cracking. The crystals were first soaked in a solution containing 0.5 mM ATP, 1 MM $MgCl_2$ for 2 hours, then crosslinked with 0.1% glutaraldehyde for 1 hour at 4° C. After extensive washing, the crystals were transferred to an inhibitor solution in 200 mM HEPES, 5% ethyleneglycol and 1% DMSO. This procedure allowed crystals to be soaked at inhibitor concentrations up to 0.2 mM for several days without showing any damage. X-ray data collection was carried out on an R-Axis II image plate detection system, mounted on a Rigaku rotation-anode generator. Data were collected under a stream of cold nitrogen (100° K.) from a single crystal in 25% ethyleneglycol. The CDK2-purvalanol B crystals diffracted as well as native, although freezing altered slightly the unit cell dimensions and increased the mosaic spread from 0.2 to 0.6 degrees. The crosslinking itself did not significantly alter the diffraction characteristics. Intensity data were processed with the programs DENZO and SCALEPACK. The program TRUNCATE, as implemented in the CCP4 suite was used to obtain the final set of structure factor amplitudes.

Refinement of the CDK2-purvalanol B complex was started from the coordinates of the highly refined CDK2-ATP model. All refinement steps were carried out using the program X-PLOR (A.T. Brüinger, Yale Univ Press, Version 3.0, 1991). Molecular replacement followed by rigid body refinement was necessary to succesfully reorient and reposition the CDK2 molecule in the unit cell of the frozen crystal. The CDK2 model was further refined using several rounds of conjugated-gradient energy minimization. At this stage the electron density corresponding to purvalanol B was clearly visible from 2fo-Fc and fo-Fc Fourier maps and the inhibitor could be added to the model. Several rounds of both X-ray restrained energy minimization and molecular dynamics in the resolution range 7–2.05 Å, alternated with model building using the program O, where necessary to improve the model. In the last rounds of refinement low resolution data were included, applying a bulk solvent correction (J. S. Jiang & A. T. Brünger, *J. Mol Biol.* 243:100 (1994)). At this point a simulated annealing omit map (A. Hodel, et al., *Acta Cryst*. A48:851, (1992)) of the inhibitor binding site indicated that a minor portion of the purvalanol B molecules were bound with their aniline rings flipped ~160 degrees (based on electron density for the 3-chloroanilino atom). The double conformation of purvalanol B was included in the refinement, lowering the $R_{free}$ by 0.5%. The final model includes 279 residues of CDK2 (residues 36–43 and 153–163 are not included because of weak or missing electron density), purvalanol B, 91 molecules of $H_2O$ and one molecule of ethyleneglycol.

The crystallography statistics for CDK-purvalanol B complex were as follows. Data: space group: P212121, cell constants (Å) a=53.55, b=71.35, c=72.00, resolution (Å) 32–2.05, Number of unique reflections=17655, completeness (%)=98.7 (91.6 from 2.11–2.05 Å), $R_{merge}$ (%)=5.5. Refinement: $R_{factor}$ (%)=18.8, $R_{free}$ (%)=26.4, average atomic B-values§ ($Å^2$) protein: 31.4, inhibitor=32.2, waters=37.7, deviations observed: rms, bond lengths, (Å)= 0.008, rms, bond angles, (8)=1.31.

The electron density showed that binding of purvalanol B to the CDK2 crystals was well-ordered except for the 3-chloroanilino group which appeared to be bound in two alternative conformations. Purvalanol B fit snugly into the ATP binding site as was evident in the 86% complementarity between the surface area buried by the inhibitor (364 $Å^2$) versus that buried in the protein (423 $Å^2$). For comparison, the corresponding values were 78% for roscovitine, 73% for olomoucine, and 81% for ATP. The overall geometry of purvalanol B bound to CDK2 resembled that of the related adenine-substituted inhibitors in the CDK2-olomoucine and CDK2-roscovitine complexes, with the purine ring and its C2, N6 and N9 substituents occupying similar binding pockets. The purine ring made mostly hydrophobic and van der Waals contacts with CDK2 residues and a pair of conserved hydrogen bonds from the N7 imidazole nitrogen to the backbone NH of Leu83 and between the N6 amino group and the backbone carbonyl of Leu83. Furthermore all three 2,6,9-trisubstituted adenines formed a hydrogen bond between the acidic C8 atom of the purine ring and the carbonyl oxygen of Glu81, an infrequently observed interaction in the crystal structures of nucleic acids and proteins (Wahl & Sundaralingam, *Trends Biochem. Sci.* 22:97–102 (1997)). This interaction was likely to be important as it partly compensates for the loss of a hydrogen bond between this atom and either the N6 amino group of ATP in the CDK2-ATP complex, or a water molecule in the unliganded CDK2 structure.

The C2-side chain of purvalanol B bound in the ATP ribose binding pocket, with the R-isopropyl group closely packed against backbone atoms of the glycine-rich loop and the hydroxyl group making a hydrogen bond with the backbone carbonyl of Gln3 1. Interestingly, the R-isopropyl side chain of purvalanol B led to a significant repositioning of the C2 substituent relative to the R-ethyl substituent of roscovitine. This repositioning left open a pocket in the active site lined by the polar side chains of Lys33, Asn132 and Asp145. Some electron density was visible in this region, most likely due to the binding of an ethyleneglycol molecule. In the CDK2-flavopiridol complex, this region was occupied by the N-methylpiperidinyl ring of the inhibitor, making favorable interactions with the polar residues. Further improvements in affinity resulted from contacting the polar residues Lys33, Asn132 and Asp145 with substituents appended from the C2 nitrogen, or by extending the side chain emanating from the chiral center.

Like the benzylamino group in olomoucine and roscovitine, the 3-chloroanilino group at N6 of purvalanol B pointed towards the outside of the ATP-binding pocket and occupied a region not occupied by any parts of the ATP in the CDK2-ATP complex. Interactions in this region were largely responsible for the increased affinity and selectivity of the inhibitors compared to ATP, as was further demonstrated by the binding of flavopiridol, whose phenyl ring is also bound here. In the CDK2-purvalanol B complex, the 3-chloroanilino group of the inhibitor is bound at a slightly different position compared to the benzylamino groups in CDK2-olomoucine and CDK2-roscovitine, allowing for an optimized packing of the phenyl ring against the side chains of Ile10 and Phe82. Further stabilization of the binding of the 3-chloroanilino group came from a hydrogen bond with the side chain of Asp86, which existed in about two thirds of the molecules in the CDK2-purvalanol B crystals. In the other conformation, the phenyl ring of the 3-chloroanilino group was flipped approximately 160 degrees with the chlorine atom located at the opposite site, away from the carboxylate group of Asp86. This ambiguity in binding mode of purvalanol B suggested a partially protonated state of Asp86. The increased binding affinity of purvalanol B arose in part from entropic forces due to the steric constraints imposed by the purine and chlorinated aniline ring systems that limited the number of conformations of the inhibitor. In contrast, the sixfold improvement in $IC_{50}$ resulting from the chlorine substitution on the phenyl ring of flavopiridol most likely resulted from improved packing interactions. Numerous substituents at the 4-position of the aniline ring were tolerated, consistent with the solvent accessibility of this site in the crystal structure, making this position an obvious candidate for altering both the solubility and membrane permeability. The N9 substituents of the three adenine-substitued inhibitors bound in a small hydrophobic pocket formed by the side chains of Val118, Ala31, Phe80, Leu134 and Ala144. Binding was most favorable for the isopropyl group of purvalanol B and roscovitine, whereas the methyl group of olomoucine was found to be too small to occupy the pocket completely.

Example 10

Example 10 shows cellular effects of inhibition by purines and flavopiridol.

Figure 4D:
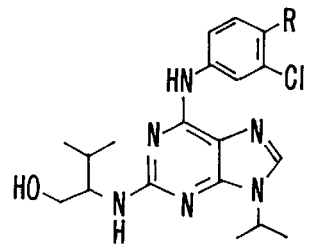
FIG. 4D purvalanol A and B.
Figure 4E:
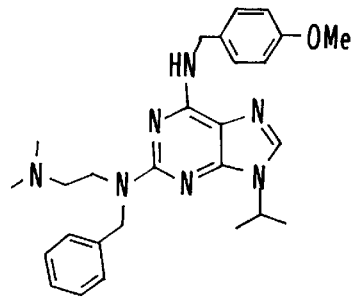
FIG. 4E inhibitors of Jun kinase (JNK)
Figure 4F:
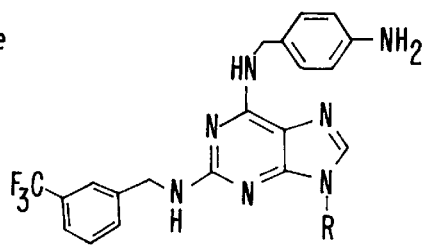
FIG. 4F compounds 100 and 101.

The differences in the cellular effects of purvalanol A and flavopiridol, despite their apparent in vitro specificity for CDK2, led to further comparisons of the modes of action of these two compounds. The cellular effects of the compounds were determined by measuring changes in mRNA levels in yeast following treatment with compounds. mRNA transcript profiles were obtained in Saccharomyces cerevisiae because of the availability of high density oligonucleotide expression arrays (Lockhart, et al., Nat. Biotech. 14:1675–1680 (1996); and Wodicka, et al., Nat. Biotech. 15: 1359–1367 (1997)), and because the yeast cyclin dependent kinase (CDC28) is highly homologous to human CDK2. The use of high density oligonucleotide probe arrays (DeRisi, et al., Science 278:680–686 (1997)) made it possible to measure quantitatively and on a genome-wide scale, mRNA levels following chemical, environmental or genetic perturbation. A close analog of purvalanol A with enhanced solubility [(2-(2-hydroxyethyl)-6-(3-chloroanilino)-9-isopropylpurine (compound 52)] and flavopiridol were profiled (FIG. 4D). Purvalanol A was shown to be an effective inhibitor of yeast Cdc28p with an $IC_{50}$ of 80 nM.

Because of weak inhibition of yeast growth by flavopiridol, a strain was employed with three drug sensitizing deletions (erg6, pdr5, snq2). This strain showed 50% growth inhibition (GIo) for compound 52 and flavopiridol at concentrations of 20 $\mu$M and 7 $\mu$M, respectively. Three cultures (110 mL, YPD) were inoculated with single colonies of YRP1 (MATa, erg6::LEU2, pdr5::TRP1, snq2::HIS6) and grown at 30° C. with constant agitation in a water bath incubator. When cell density reached an optical density of 0.9 (600 nm), 27.5 $\mu$L of a 100 mM DMSO stock solution of compound 52, flavopiridol, or DMSO alone was added. After two hours, the cells were harvested by centrifugation and flash frozen with liquid nitrogen. For the temperature sensitive cdc28 mutants, three cultures (75 mL, YPD) of AFS199 (cdc28-13), AA 104 (cdc28-4) and their isogenic background AFS34 (MATa, ade2-1, his3-11, leu2-3, trp1-1, ura3) were grown from single colonies to an O.D. of 0.9 (600 nm) and harvested as described above. Frozen cells were stored at –80° C.

Yeast cultures were grown to late log phase and treated with 25 $\mu$M concentrations of the inhibitors for two hours after which cellular poly (A)+ mRNA was isolated and converted to biotin-labeled cRNA. The labeled cRNA was then hybridized to a set of four arrays containing more than 260,000 25-mer oligonucleotides. The identities of open reading frames (ORFs) were obtained from the following public databases: Yeast Protein Database (quest7.proteome.edu) and Saccharomyces Genome Database (genome-www.stanford.edu). Transcripts that showed a significant and reproducible change in concentration (two to three-fold) in cells treated with the two compounds between three independent hybridizations were examined further.

Out of more than 6200 genes monitored, 335 (5% of transcripts) and 267 (4% of transcripts) showed a greater than three-fold change in transcript levels when treated with compound 52 and flavopiridol, respectively. In each instance, only approximately 10% of the genes affected were down-regulated. In particular, of the 105 transcripts that changed in response to both compounds only four were down regulated, all of which (CLB1, HTA1, HTA2, EGT2) were associated with the cell cycle progression and could be attributed to Cdc28p inhibition. The transcript encoding CLB1 ($G_2$ cyclin implicated in transition into mitosis) showed a significant decrease, consistent with the requirement of CDK activity for efficient transcription (Cross, Curr. Opinion. Cell Biol. 7:790–797 (1995)). Similarly, CDK activity has been implicated in transcriptional regulation of histone genes such as HTA2 and HTB2 (Van Wijnen, et al., *Proc. Nat'l Acad. Sci. USA* 91:12882–12886 (1994)) and EGT2, a gene involved in the timing of cell-separation after cytokinesis. Other genes involved in cell cycle progression such as YDR247 (a putative negative regulator of meiosis), RAD16 (involved in $G_2$ repair of inactive genes), YBR214 (similar to the moc1 protein of *S. pombe* which is involved in meiosis and mitosis) and RLM1 (a target of Mpk1p which is regulated by Cdc28p kinase activity) were induced. The changes in expression levels of these genes are consistent with predominant $G_1/S$ inhibition, in accord with FACS determined DNA content measurements previously reported for analogous purine derivatives (Brooks, et al., *J. Biol. Chem.* 272:29207–29211 (1997)).

Compound 52 and flavopiridol also had similar effects on the transcript levels of many genes involved in cellular metabolism. For example, genes that are involved in glycolysis (PDC5, PFK26, YAL061W, an alcohol dehydrogenase), the citric acid cycle (ALD4, ALD5), glycogen metabolism (PGM2, YPR184W, a putative debranching enzyme), gluconeogenesis (PCK1) and a probable sugar transporter (HXT5) were induced. Other changes in transcript levels common to both compounds and therefore likely to be associated with drug exposure, included up-regulation of a number of genes encoding members of the ATP-binding cassette (ABC) superfamily and other transport proteins (PDR10, PDR15, SNG1), proteins involved in cell wall biosynthesis (ECM3 relatives), including ones implicated in increased drug resistance (GSC2) (Mazur, et al., *Mol. Cell Biol.* 15:5671–5681 (1995)), genes involved in vacuole endocytosis and regulation (YPT53, PMC1), glutathione-dependent detoxification proteins (ROD1 relatives, TSA1 relatives, glutathione transferase homologs), and several heat shock genes (HSP30, HSP82, HSP104, SSE2). Additional common changes induced by the compounds involved, for example, a GTP/ATP binding protein (YDL223) that putatively binds microtubules, the actin binding protein ABP1, and forty genes of unknown function.

Although cdc28p was the intended target of both compound 52 and flavopiridol, more than half of the changes in transcript levels that resulted from exposure to the two compounds were distinct. For example, of the approximately fifty genes whose transcript levels were decreased at least three-fold in response to compound 52, fourteen were ribosomal proteins (including RPL4A, RPL26B, RPS24A). This was found to be consistent with the observed up regulation of protein kinase A, which has an established role in modulating ribosomal protein synthesis (Griffioen, et al., *FEMS Microbiol. Lett.* 123:137–44 (1994)). In contrast, no ribosomal protein transcript levels decreased more than three-fold for flavopiridol. Compound 52 also uniquely affected YMR116C (a determinant of cell size), a cytosine/purine permnease and CLB2 ($G_2$/M-phase specific cyclin). Among the genes flavopiridol uniquely induced are YMR276W, which encodes a ubiquitin like protein involved in duplication of the spindle pole body and CLN2, which encodes a $G_1/S$ specific cyclin. These results suggested that these two compounds may inhibit cdc28p function or affect pathways involving cdc28p kinase activity to different degrees. Alternatively, the differential effects of the two compounds resulted from different cellular bioavailability or their effects on other cellular targets not specifically examined in vitro such as the additional yeast CDKs KIN28 (involved in mRNA transcription) and PHO85 (phosphate regulation).

Given the large number of transcripts that were differentially affected by these two CDK inhibitors, the transcriptional consequences of a genetic mutation in the Cdc28p kinase were examined. Approximately 100 mRNAs in the cdc28-4 strain exhibited more than two-fold inductions over wild type, consistent with the greatly diminished Cdc28p kinase activity at the permissive temperature (Figure X). Interestingly, very few of the cell cycle associated genes that changed in response to flavopiridol or compound 52 were affected in this mutant (Koch & Nasmyth, *Curr. Opinion. Cell Biol.* 6:451–459 (1994)). Instead, as with flavopiridol and compound 52, a number of metabolic genes involved in glycogen synthesis, the citric acid cycle, gluconeogenesis and the glyoxylate cycle were induced. Consistent with these changes is the strong induction of the HAP4 transcription factor, which has been implicated in regulating many respiration genes (Russell, et al, *Mol. Biol. Cell* 4:757–765 (1993)). Another class of transcripts induced in cdc28-4 were ones involved in stress signaling (Ruis & Schuller, *BioEssays* 17:959–965 (1995)): heat shock elements (HSEs), stress response elements (STREs), and members of the major facilitator superfamily (MFSs). The transcriptional responses to this single point mutation in CDC 28 were interpreted as cellular responses that mitigated the effects of this alteration. Complete inactivation of Cdc28p kinase activity resulted in more cell cycle related transcript changes but in addition, a host of alterations associated with cell cycle arrest and secondary consequences of heat shock (required to induce arrest) appeared.

Transcript profiles were also carried out in the cdc28 temperature sensitive allele cdc28-13. The cdc28-13 strain contains an arginine to asparagine mutation at residue 283 near the C-terminus which does not significantly affect kinase activity at the permissive temperature but does cause cell cycle arrest when switched to the nonpermissive temperature (LoRincz & Reed, *Mol. Cell Biol.* 6:4099–4103 (1986)). The cdc28-13 strain showed very few changes in mRNA transcripts when compared to wild type at the permissive temperature. The levels of only 11 mRNAs changed by more than two-fold, consistent with the observation that this mutant possesses essentially wildtype kinase activity at 25° C. In addition, the nearly identical gene expression patterns obtained for the cdc28-13 and isogenic wildtype CDC 28 strain demonstrate the reproducibility of these experiments.

Since CDC 28 is an essential gene, the transcript profile of two cdc28 temperature sensitive strains (cdc28-4 and cdc28-13) and their isogenic wild-type (wt) strains were measured under permissive growth conditions (25° C). Under these conditions cdc28-4 grew at essentially wild type rates which approximated the small degree of growth inhibition observed for the two hour compound treatments used to prepare the inhibitor profiles. The cdc28-4 strain contains a single histidine to tyrosine mutation at position 128 which when mapped onto the human CDK2 crystal structure is located adjacent to the ATP binding site. Although cdc28-4 cells grow at essentially wildtype rates under permissive conditions, Cdc28p specific kinase activity is greatly reduced as measured by an immunoprecipitation phosphorylation assay (Reed, et al., *Proc. Nat'l Acad. Sci. USA* 82:4055–4059 (1985)). When switched to the nonpermissive temperature, the cdc28-4 mutant arrests early in the cell cycle as large unbudded cells. Since Cdc28p activity is high during S phase and mitosis, the mutation in cdc28-4 might be expected to simulate the effects of chemically inhibiting the kinase during these two key points in the cell cycle. However, the specific mechanism of Cdc28p inactivation may differ significantly from that resulting from a competitive active site inhibitor.

When the changes in mRNA levels for the cdc28-4 mutant were compared to the changes resulting from exposure to the two compounds, considerable overlap was apparent: of the 100 significant transcriptional changes observed for cdc28-4, 50 were also observed for the two compounds (10 exclusively for compound 52, 12 exclusively for flavopiridol, and 28 that responded to both compound 52 and flavopiridol). The set of overlapping genes included virtually all of the transcription factors and many of the metabolic, biosynthetic, stress response, and unknown genes. However, there were also a number of genes in these categories that only showed significant changes for the cdc28-4 mutant, including a protein with similarity to members of the major facilitator superfamily (YOL158C), metabolic genes (MDH2, CIT1), and a variety of proteins of unknown function. There was also a large set (approximately 80) of transcripts including the down regulated cell cycle transcripts discussed earlier that showed a greater than 3-fold response to both compounds but were absent in the cdc28-4 response.

The absence of changes in mRNA levels for other cell cycle genes in the cdc28-4 profiles and the partial overlap of the mutant and compound transcript profiles reflected the inherent differences between chemical and genetic methods for disrupting cellular processes. This was due to the greater specificity associated with genetic mutations versus chemical inhibition, differences in the mechanisms of inhibition, and the ability of a cell to adapt to nonlethal genetic changes in ways that were different from those induced by chemical inhibition. The strategy of comparing changes in transcript levels resulting from gene mutations to those obtained in the presence of a drug to identify targets proved to be simpler for a less central target that would give a more characteristic "signature" pattern.

Example 11

Example 11 demonstrates screening purine libraries against other cellular targets.

To determine whether libraries constructed on a purine scaffold might provide a general source of lead structures for the development of selective and potent inhibitors of other cellular targets, purine libraries were screened against a series of other kinases. Screening had previously resulted in selective inhibitors for glycogen synthase kinase (GSK) (Woodgett, et al., *Trends Biochem. Sci.* 16:177–81. (1991)) and Jun kinase (JNK). JNK is a member of the MAP kinase family that activates transcription factor c-Jun in response to pro-inflammatory cytokines and enviromental stress (Karin. *J. Biol. Chem.* 270:16483–16486, (1993)). Despite the observed activation of JNK in response to a multitude of extracellular stimuli, its exact physiological functions remain unclear. Inhibitors that could specifically block JNK mediated signal transduction without affecting other MAP kinases, would be very useful in elucidating the physiological functions of JNK.

The recombinant JNK-his6 fusion was produced in *E. coli* and purified by Ni-agarose chromatography. A 30 µL kinase reaction contained 20 mM $MgCl_2$, 20 mM Tris/HCl pH 7.6, 20 µM ATP (cold), 66 nM JNK, 0.5 µL $\gamma$-$^{32}$P-ATP, 1 µg GSTc-Jun(1–79), and the indicated concentrations of inhibitors. The reaction was carried out at 30° C. for 30 min. The phosphorylated GSTc-Jun was separated by SDS-PAGE, and phosphorylated bands were quantified by phosphoimager analysis.

Screening of a collection of 2,9-substituted-6-(4-aminobenzylamino) purines using an in vitro phosphorylation assay yielded a number of compounds that were active in the 1–10 µM range. Several of these compounds (100, 101, FIG. 1), were specific JNK inhibitors, as the related MAP kinases p38 and ERK were unaffected at inhibitor concentrations up to 100 µM.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purpose.

What is claimed is:

1. A method of determining the identity of proteins that modulate cell proliferation during or after exposure to chemical or genetic changes, said method comprising isolating mRNA transcripts generated from cells after exposure to a compound known to modulate cellular proliferation by hybridizing under stringent conditions to at least one oligonucleotide complementary to a nucleic acid sequence which encodes a protein associated with cell proliferation, isolating mRNA transcripts generated from cells not exposed to said compound by hybridizing to the oligonucleotides, comparing the total number of mRNA transcripts from both treatedand untreated cells, and determining which proteins are encoded by mRNA transcripts present in differing amounts in treated or untreated cells, wherein said compound has the following structure:

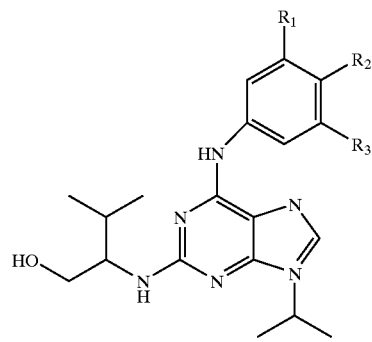

wherein $R_1$ is selected from the group consisting of H and $NH_2$; $R_2$ is selected from the group consisting of H, $CO_2H$, OH and halogen; and $R_3$ is selected from the group consisting of $CO_2H$, $NH_2$ and halogen.

2. The method of claim 1 wherein the mRNA transcripts are cRNA.

3. The method of claim 1 wherein oligonucleotides are about 15 to about 50 nucleotides in length.

4. The method of claim 3, wherein the oligonucleotides are linked to a solid support in a high density array.

5. The method of claim 1, wherein said compound is NG-56, having the following structure:

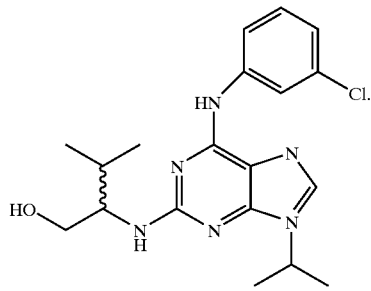

6. The method of claim 1, wherein said compound is NG-60, having the following structure:

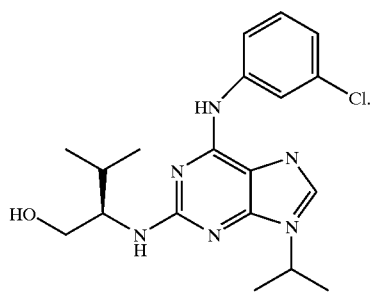

7. The method of claim 1, wherein said compound is NG-94, having the following structure:

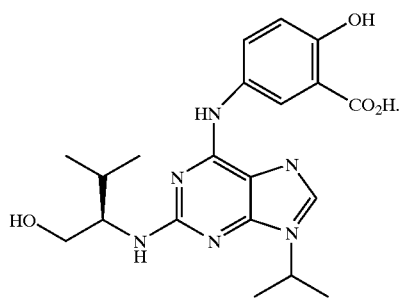

8. The method of claim 1, wherein said compound is NG-95, having the following structure:

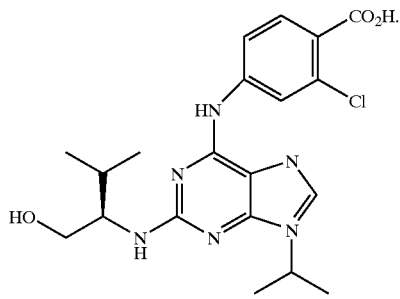

9. The method of claim 1, wherein said compound is NG-96, having the following structure:

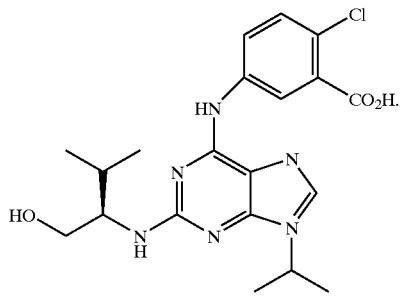

10. The method of claim 1, wherein said compound is NG-97, having the following structure:

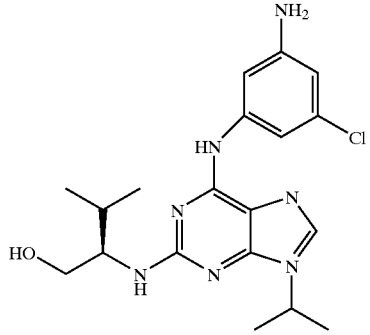

11. The method of claim 1, wherein said compound is NG-98, having the following structure:

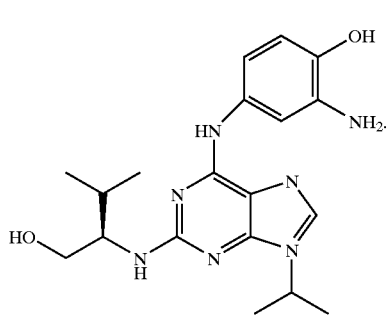

* * * * *